United States Patent [19]

Garfunkel et al.

[11] 4,244,650
[45] Jan. 13, 1981

[54] AUTOMATIC OPTICAL INSPECTION AND SORTING

[75] Inventors: James H. Garfunkel, Mound; Kenneth P. Koeneman, Lakeville, both of Minn.

[73] Assignee: Honeywell Inc., Minneapolis, Minn.

[21] Appl. No.: 898,221

[22] Filed: Apr. 20, 1978

[51] Int. Cl.³ .......................... G06K 9/38; G06K 9/82; G06K 9/46; G01B 11/00
[52] U.S. Cl. ................................. 356/71; 250/223 B; 356/394
[58] Field of Search ............... 356/71, 446, 448, 394; 250/223 B, 255, 257, 202; 340/146.3 Q, 146.3 AC

[56] References Cited

U.S. PATENT DOCUMENTS

| | | | |
|---|---|---|---|
| 3,724,923 | 4/1973 | Fischer | 356/152 |
| 3,956,629 | 5/1976 | Gomm | 250/223 R |
| 4,047,000 | 9/1977 | Bryant et al. | 250/223 B |
| 4,175,236 | 11/1979 | Juvinall | 250/223 B |

Primary Examiner—Conrad J. Clark
Assistant Examiner—Wm. H. Punter
Attorney, Agent, or Firm—Omund R. Dahle

[57] ABSTRACT

In this disclosure is described apparatus for automatic pattern or object recognition in which objects or goods with optically recognizable patterns are optically scanned for the pattern by passing the objects in front of optical sensor means where the light reflected from the object is received by the sensor means. In this disclosure there is described in detail apparatus for identifying and sorting various types of returnable bottles such as soft drink bottles by scanning across the bottles, the light reflected from the bottle graphics providing a coded signal or signature representing the bottle type. The identification is accomplished by considering such signature features as number of peaks, largest gap, area under curve, summation of difference between consecutive data points and the ratio of the area to the difference summation. The values obtained for the features are then matched with known feature bounds to provide the identification.

4 Claims, 23 Drawing Figures

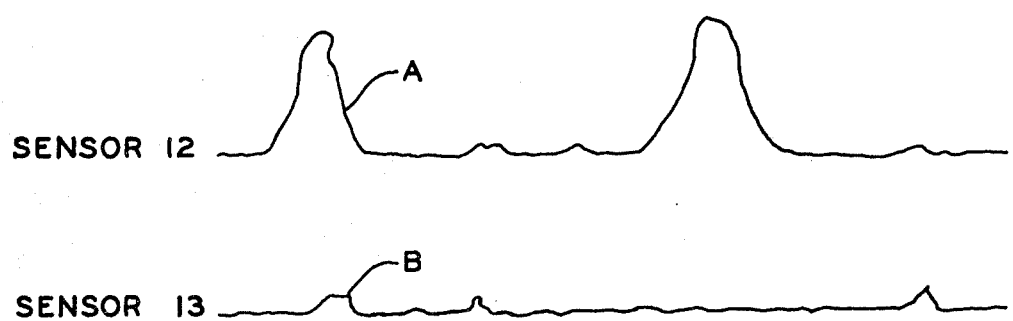
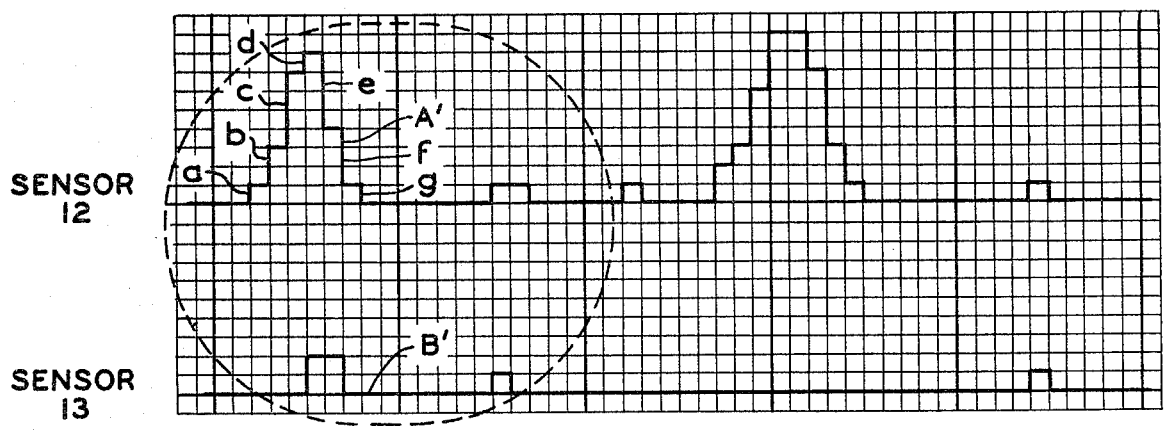
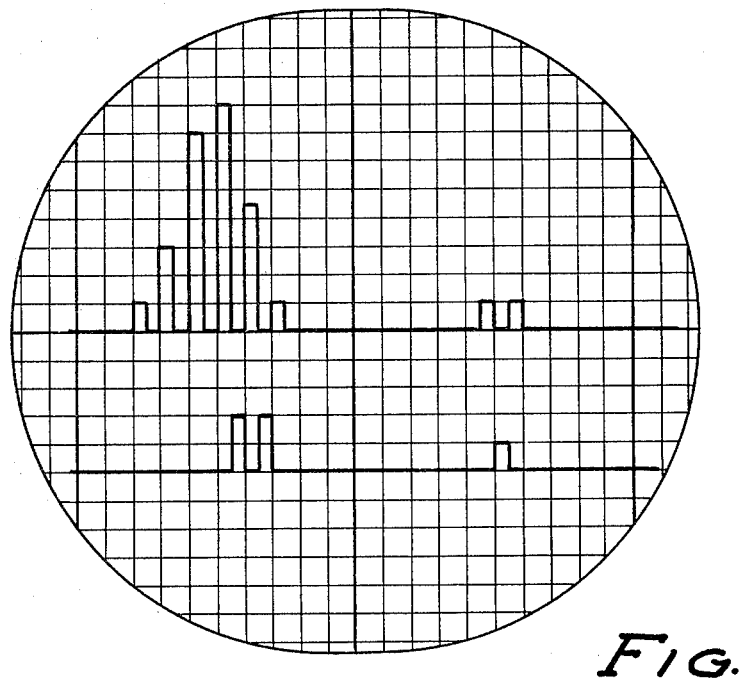

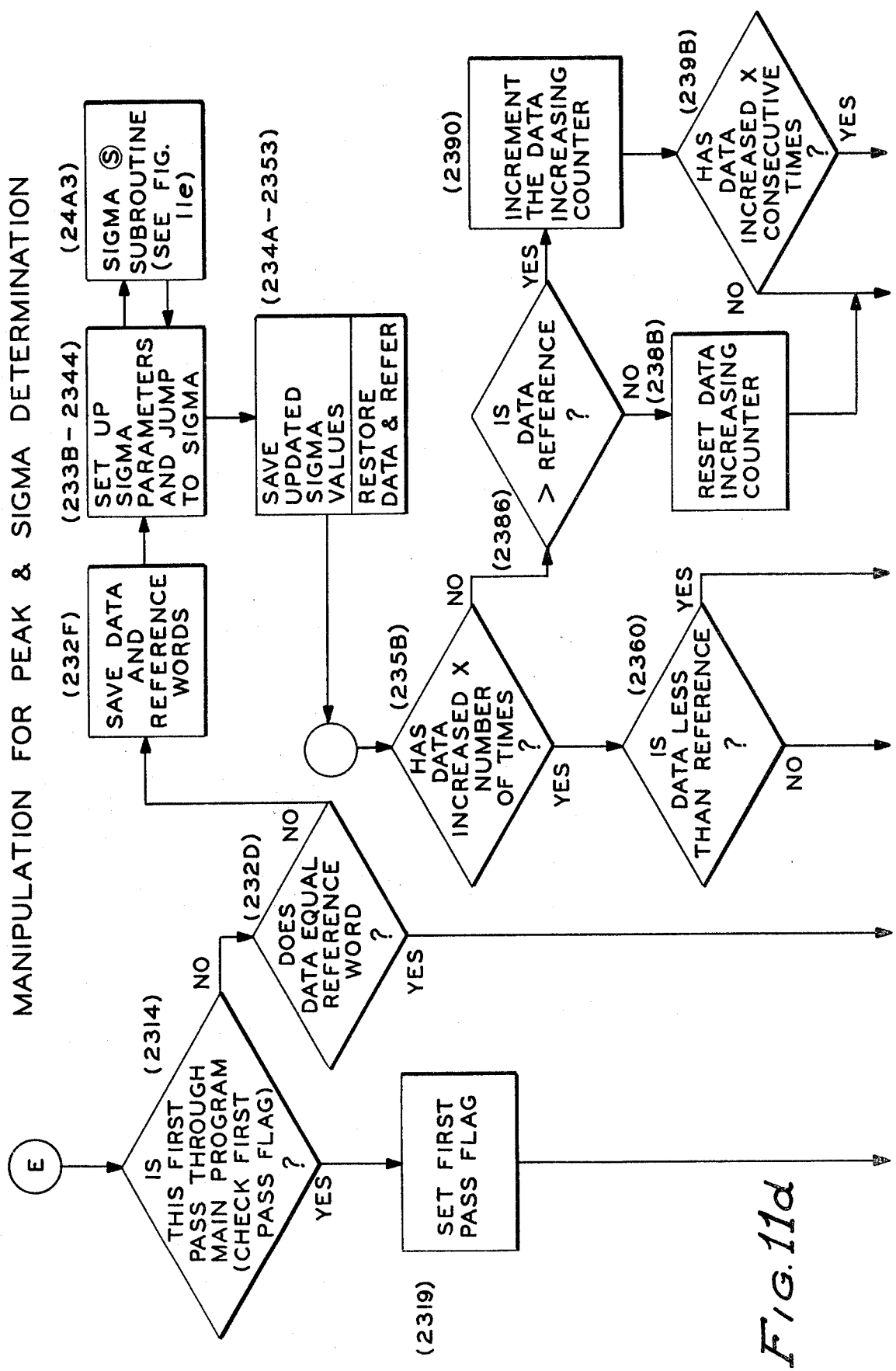

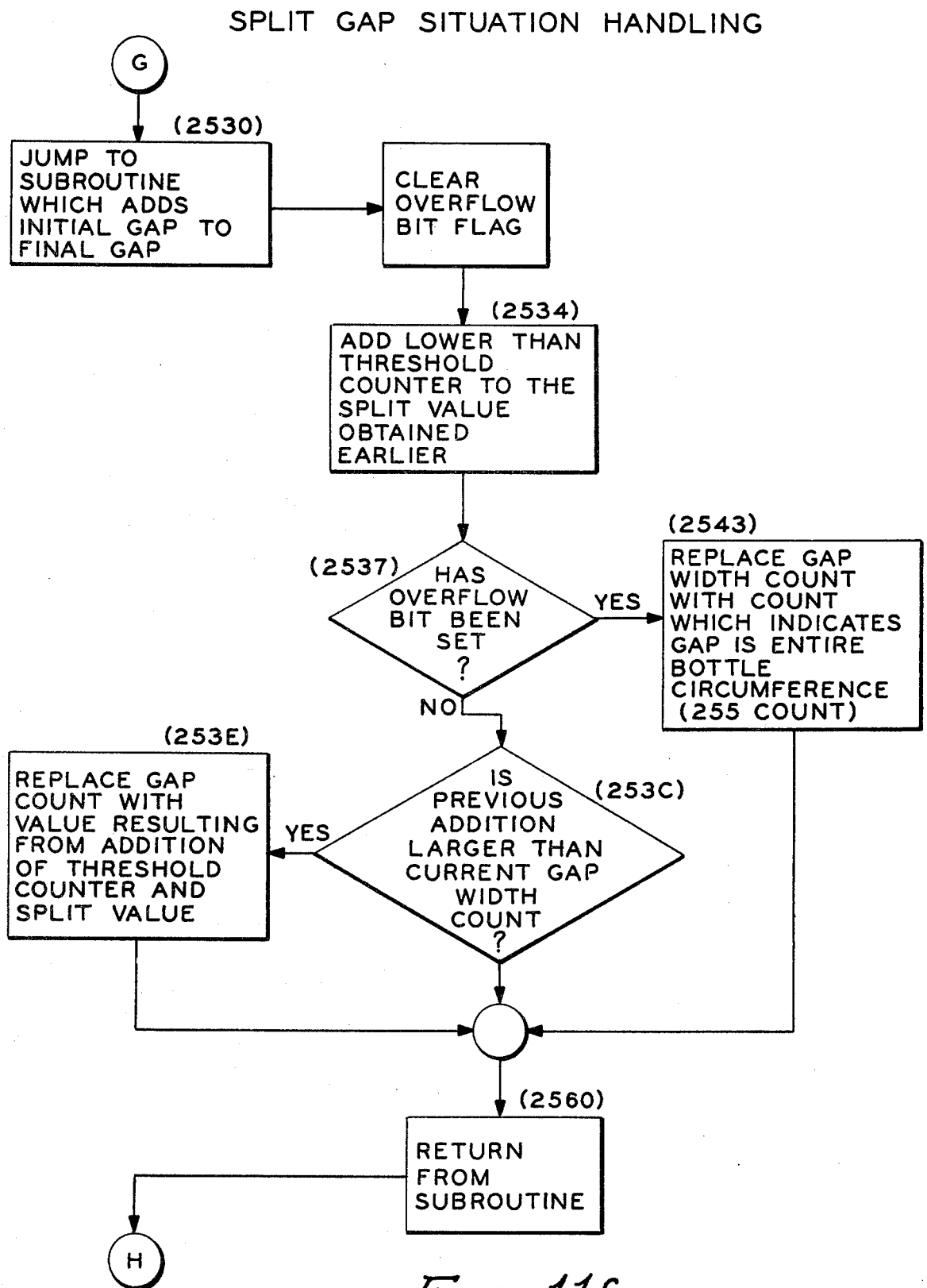

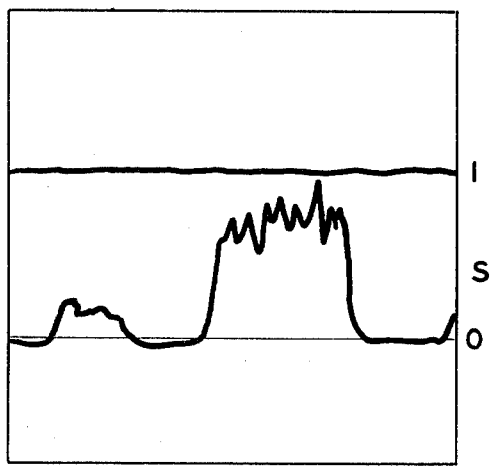
ORANGE CRUSH
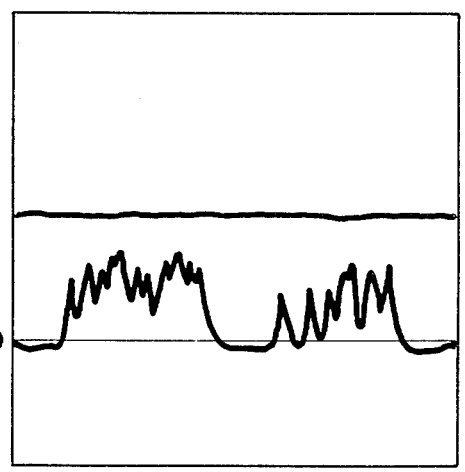
COCA COLA
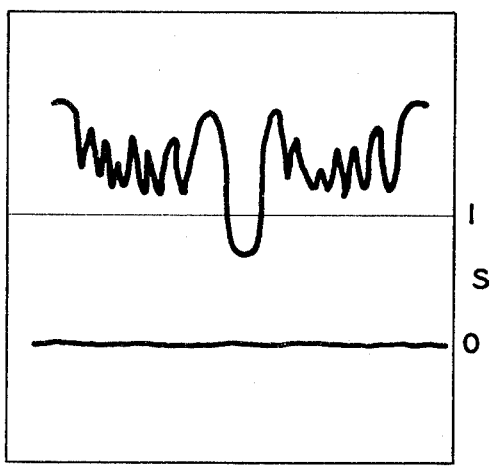
FRESCA
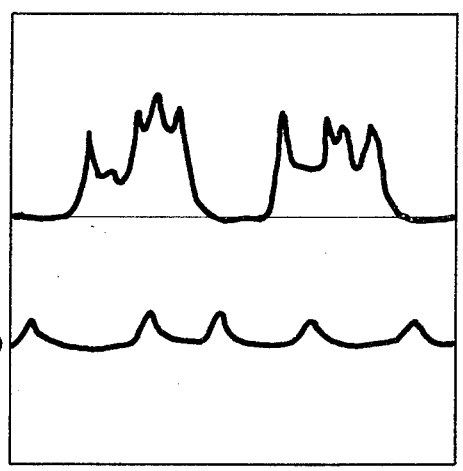
TAB
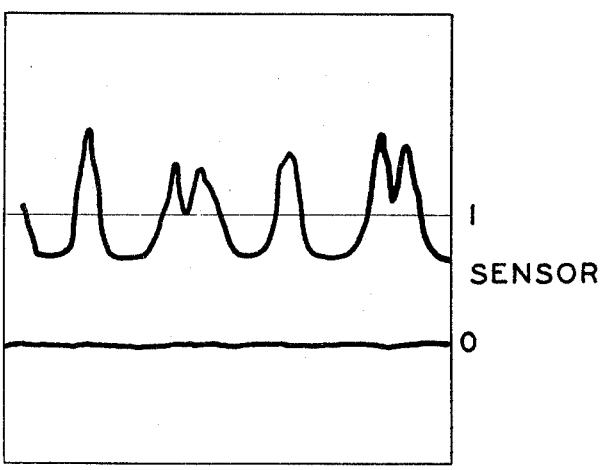
SPRITE
FIG. 13 ered cans, fabric patterns and the like. In a specific embodiment described this invention relates to automatic identifying (sorting and separating) of different types of returnable bottles such as soft drink bottles. Refillable soft drink bottles which are returned to the bottler are previously sorted by size but not by type. This invention allows an automatic identifying by type.

AUTOMATIC OPTICAL INSPECTION AND SORTING

FIELD OF THE INVENTION

This Invention relates generally to optical pattern recognition of goods such as bottles, labelled cans, fabric patterns and the like. In a specific embodiment described this invention relates to automatic identifying (sorting and separating) of different types of returnable bottles such as soft drink bottles. Refillable soft drink bottles which are returned to the bottler are previously sorted by size but not by type. This invention allows an automatic identifying by type.

BACKGROUND OF THE INVENTION

With the increasing use of refillable containers, there is an expanding need in the soft drink industry for means of sorting bottles which are returned, so that the correct product goes into the proper bottle. At the present time, despite attempts to automate sorting in the past, sorting remains a manual operation at the bottling plant. Direct cost reduction to the bottler is possible by automating the sorting process. Examples of earlier patent art which have dealt with this problem in some form are U.S. Pat. Nos. 3,089,594, 3,228,520, 3,248,845, 3,257,897, 3,265,901, 3,351,198, 3,358,552, 3,529,169, 3,589,513, 3,955,179, 3,956,629 and 4,047,000.

SUMMARY OF THE INVENTION

In the present invention which relates generally to optical pattern recognition of goods, an embodiment is described of a system which is capable of automatically identifying soft drink bottles in a non-contact sensing arrangement, without the need for a change in the bottle graphics. The sensing uses a scan line across the graphics on the bottle. The electro-optic sensing means comprises an light-emitting diode and silicon photo detector used in a reflective mode. The bottle is rotated in front of the sensor, and the different reflectance of the graphics (label) from that of the glass produces a varying signal which is characteristic of the type of bottle. A programmed microprocessor classifies the bottles as to type.

In the general operation of the bottle sorter apparatus, the individual bottles to be identified are moved in a single file by the bottle advancing conveyor into the inspecting area. At this point, each bottle is spun or rotated on its axis while the photo transistor senses the reflected radiation from the surface of the bottle for a full rotation and the bottle is identified. The identified bottle as it moves downstream from the inspecting station of the conveyor is then selectively shunted off the conveyor to the proper area for that type of bottle.

BRIEF DESCRIPTION OF THE DRAWINGS

FIG. 4 is a graphical description of the analog output of the two sensors of FIG. 3.

FIG. 5 is a graphical description of the digitized signals of FIG. 4, and FIG. 5a is an expanded view of a section of FIG. 5.

FIG. 13 shows the pattern received from several common bottles.

DESCRIPTION

In this invention, bottles are identified by direction light towards the bottle graphics, rotating the bottle 360° and detecting reflected radiation, the reflected signature of the bottle providing identity. Particularly our identification of empty soft drink bottles is accomplished by analyzing the digital representations of discrete reflectance measurements in one or two circumferential bands at label level. The identification is accomplished by considering such signature features as number of peaks, largest gap, area under curve, summation of difference between consecutive data points, and the ratio of the area to the difference summation. The values obtained for the features are then matched with known feature bounds characteristic of each bottle to be identified.

Figure 1:
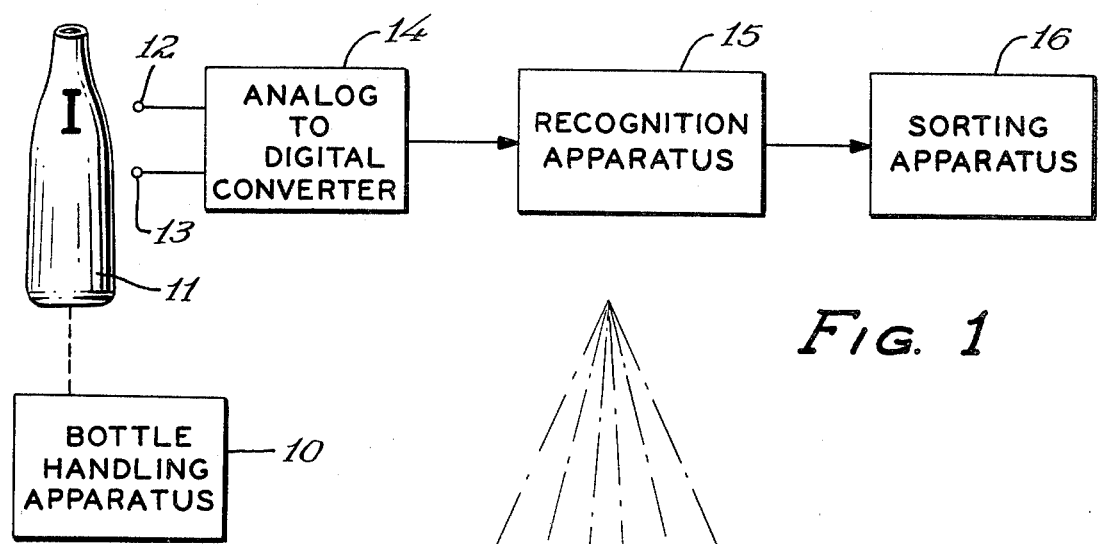
FIG. 1 is a much simplified block diagram of the system of the invention.

Referring now to FIG. 1 which is a simplified functional block diagram, a bottle handling apparatus 10, which may comprise a conveyor system, transports a "BIG I" bottle 11 to a bottle identification area adjacent sensor means 12 and 13. BIG I is a simplified design for illustrative purposes. The sensor means each comprise a LED-phototransistor assembly. The LED (light emitting diode) illuminates the bottle adjacent the sensor with a beam of light. Light which is reflected from the bottle is sensed by the photo-transistor sensor which then provides an analog electrical output of a magnitude which is a function of the intensity of the reflected light. The bottle handling apparatus rotates the bottle while the bottle is in the identification area to produce an analog signature of the bottle reflection. The analog signal is connected to an analog-to-digital converter 14. The digital output signature is connected to recognition apparatus 15 which matches the features of the bottle with known feature bounds. The recognized bottle 11 is then directed to the proper location by sorting apparatus 16 which receives instruction from the recognition apparatus 15. Although in FIG. 1 the pattern to be recognized or identified is shown in the form of a bottle 11 which has an identifiable pattern thereon such as the bottle graphics, it is to be understood that the invention relates to optical pattern recognition generally and the object or goods having a pattern to be recognized is not intended to be limited to bottles and may include goods which are generally planar in surface as well as those which are like a bottle or a can, (i.e., generally or somewhat cylindrical). In FIG. 1 the item to be identified may be conveyed or translated past the sensor means without any rotation, if desired, as in the case of planar patterns. If a generally cylindrical item is to be identified it can preferably be rotated, or if it is properly oriented it can be conveyed past the sensor without rotation.

Figure 2:
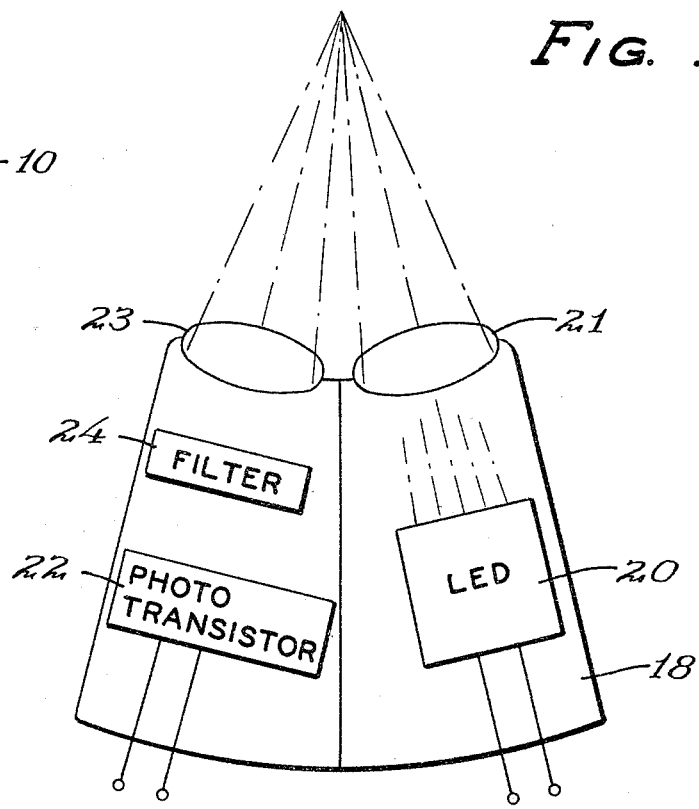
FIG. 2 is a diagrammatic representation of the sensor assembly.

In one embodiment, each of the sensor means 12 and 13 comprises an assembly 18 shown schematically in FIG. 2 including an infrared LED 20, a focussing lens 21 for the LED, a photo-transistor detector 22 responsive to infrared, a focussing lens 23 for the photo-transistor, an infrared filter 24 to minimize the effect of ambient light or the photo-transistor. The assembly may be, for example, a Spectronics Type 1404-3 assembly. The LED 20 and the photo-transistor 22, together with their lenses are canted toward each other in the assembly so that the assembly has a common focal point of the LED and the photo-transistor about 0.2" in front of the assembly. The light source and the light detection may be separate elements, if desired, rather than an assembly.

Although the embodiment described for the sensor means is infrared responsive, it may be desirable when viewing reflection from certain colors of bottle graphics to utilize a different light such as a green LED a red LED or a yellow LED. The specified LED-phototransistor assembly described is illustrative and is not intended to be limiting. The use of the word light in this document is intended to include the infrared spectrum.

Figure 3:
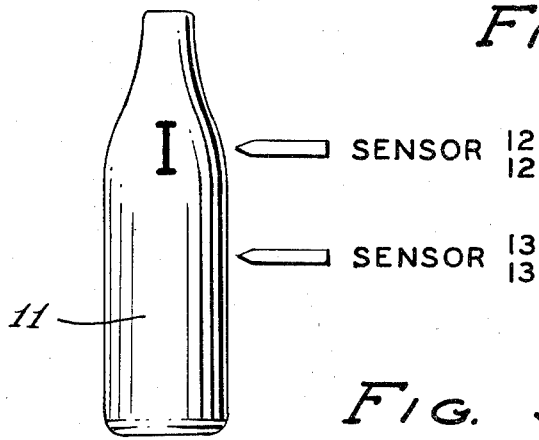
FIG. 3 is a diagrammatic representation of a sample bottle to be identified with two sensors, one viewing reflections from the graphics of the bottle.

In FIG. 3 there is shown again the BIG I bottle 11 and the sensors 12 and 13 which provide analog outputs of the reflected signal when the bottle is rotated one revolution. The BIG I bottle 11 represents a bottle on which the only graphic feature (i.e. label) is a block I, which appears on opposite sides of the bottle and which graphic is seen only by the upper sensor. FIG. 4 shows graphically such a pair of signals with curve A representing the output of sensor 12 and curve B representing the output of sensor 13. FIG. 5 shows graphically the signals in digital form after being converted by the A-D converter, with curve A' being the digital form of curve A and with curve B' being the digital form of curve B. It will be noted that with the BIG I bottle the sensor 12 crosses the bottle graphics and sees the major reflected signal while sensor 13 sees essentially no signal.

FIG. 5 is shown with a vertical scale of 10 and a horizontal scale of 54. This is a somewhat simplified digital representation for descriptive purposes and is not intended to be limiting. In one successful embodiment of this invention the actual vertical scale is 0–31 and the horizontal scale is 512. In addition, the exact wave shape of the digital signal may vary from that shown in FIG. 5 and may be more like that shown in FIG. 5a which is an expanded and more exact representation of a portion of FIG. 5.

Figure 6:
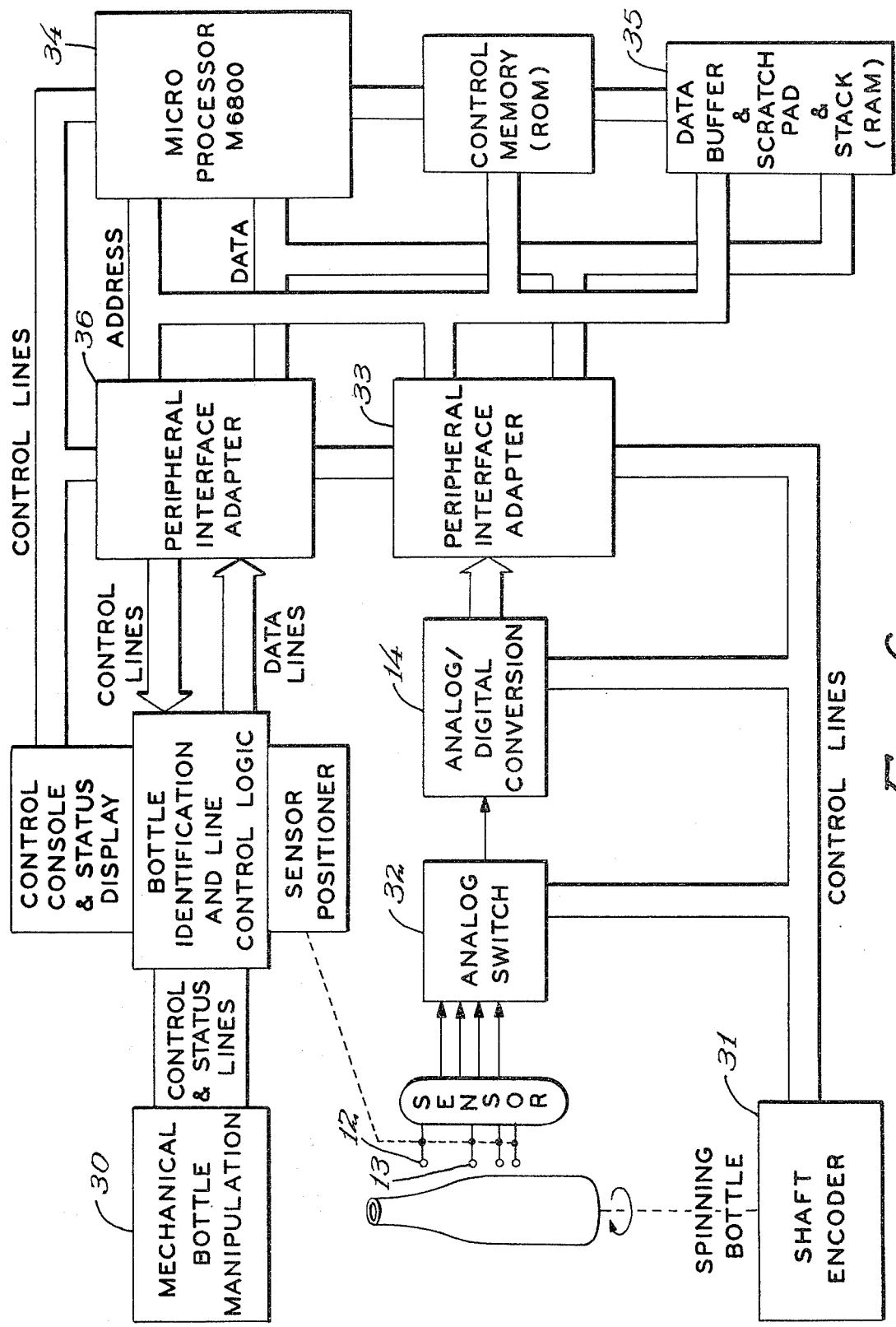
FIG. 6 is a block diagram in more detail.

FIG. 6 discloses a more detailed functional block diagram of the overall system for sorting bottles. In this Figure, the bottle handling apparatus is shown as mechanical bottle manipulation apparatus 30 and a shaft encoder 31. The bottle manipulation apparatus includes bottle spinning means at the location of the sensors. In a laboratory prototype the bottle is placed in a fixture which causes rotation of the bottle by means of a D.C. motor, such as a Honeywell model HSM3D DC motor. The rotation rate is variable and is capable of spinning the bottle at rates greater than 1800 rpm. The two LED-phototransistor sensor pairs are mounted so that their height above the base and distance from the bottle may be adjusted. The sensor may be set to receive the reflections perpendicular to the bottle surface or may preferably be canted to view the approaching or receding bottle horizon. This canting of the sensors has the effect of eliminating much of the spiked pulses due to irregularities in the bottle glass occurring when the sensor is directly perpendicular to the bottle's surface. Both sensors in the preferred embodiment are canted in this fashion. In this way, the detector receives light which is diffusely reflected from the graphics, but not the light which is specularly reflected from the glass surface.

The shaft of the drive motor is linked to the bottle as well as optical shaft encoder 31. The particular encoder (a Hutchinson Industrial Corp. 2300 series shaft encoder) effectively divides the circumference of the bottle into 512 segments to provide 512 output cycles per revolution. Analog reflectance measurements are made when each pulse from the shaft encoder is output. These analog values are applied to an analog switch 32 which selects the particular sensor to be read. The shaft encoder pulse also starts the analog-to-digital conversion process at converter 14. When the process is finished, the A/D converter issues an "end of conversion" signal to a peripheral interface adaptor (PIA) 33.

A flag bit is set in the PIA 33 when "end of conversion" is indicated. The microprocessor 34 senses the condition of the flag, stores the digital representation of the reflectance value in random access memory (RAM) 35, and resets the flag. This process continues until all 512 values are stored in the RAM buffer.

When the buffer is full, the program uses the data in the buffer to isolate the features used for identification. When the features have been determined, the program proceeds to identify the bottle from the characteristics of the features. The other PIA 36 in the system issues the appropriate identification and commands to the bottle handling mechanism.

OBTAINING AND STORING BOTTLE DATA

Bottle reflectance is measured by applying a fixed current to the infrared light emitting diode 20 which illuminates the bottle surface. The Darlington phototransistor sensor 32, which shares the same package 18 with the LED, provides an output voltage which is directly proportional to the bottle's surface reflectance. A filter 24 may be placed over the phototransistor aperture to remove most of the visible ambient light and its associated 60 Hz component where the 60 Hz or 120 Hz component is a source of unwanted signal.

In the present configuration, several sensors may be used and selected by the analog switch. In a current embodiment we are using data from two sensors 12 and 13. The analog switch 32 is now controlled by a flip-flop synchronized with the pulses from the shaft encoder 31 but may be controlled by the processor 34 when it is desirable to look at one particular sensor. We essentially interleave the data from each sensor in the memory buffer 35 alternately storing information from one sensor then the other for the entire circumference of the bottle.

This apparatus requires a time period of less than 10 usec for the A/D conversion, and with conversion rates of this order a successive approximation type of A/D converter is necessary. Specifically, in the present embodiment, we are using a 12-bit successive approximation A/D converter operating in the short cycle mode. Only the five most significant bits are presently used which gives a numerical range of values from 0 to 31 (0.0 volts to 5.0 volts in 0.15 volt steps). These five bits are stored in an eight bit data word in the five least significant bit positions. The most significant bit of the data word presently indicates the sensor source. The next two most significant bits are reserved for future use as sensor identifiers. When the bottle is rotating at 1800 rpm, each of the 512 segments is sampled for 65.12 usec yielding a 15.4 KHz sample rate for our system. The highest frequency in a waveform which can be reproduced qualitatively is the Nyquist frequency. This is equal to one half of the sampling rate, therefore the Nyquist frequency for our system would be 7.7 KHz. The Nyquist frequency as used in sampling theory is described, for example, in the text "Digital Processing of Signals" by Bernard Gold and Charles M. Rader, Lincoln Laboratories, MIT Series, McGraw Hill, 1969, pages 137-141. An optional low pass filter with a −3 dB frequency of no greater than 7.7 KHz may be used to remove high frequency components from the analog sensor data and still allow a faithful digital reproduction of the analog signal.

DESCRIPTION OF USEFUL BOTTLE SIGNATURE FEATURES

The bottle sorting system of this invention is based on analysis of relative signatures, in which relative signatures are defined as reflectance information read off the bottle starting at any random point. No absolute reference point is used to synchronize read out. The dimple (the molded indent) on the base of the bottle, for example, would be considered an absolute reference point. Using the relative signature allows bottle to be placed randomly under sensors and eliminates the need to orient the bottle before sensor data is read.

Primary bottle signature features to be described below in more detail are peak count, area under the signature, sigma value, largest gap, and ratio value (area/signal). Other features which also combine together with those above in determining the bottle signature include the peak spacing, the peak width (say at half-height), the number of points above some fixed number, the number of quartile crossings, the peak heights and of course, which of the detectors is giving the significant information.

PEAK COUNT FEATURE

The bottle signature will appear to have a distinctive number of peaks due to the changes in reflectance as the bottle label passes under the phototransistor sensor. Each of the 512 reflectance values read from the bottle circumference will be converted to a digital form which will be any integer value from 0 to 31 depending on the reflectance. In the system design, we arbitrarily define a peak as any continuous or monotonic increase in ineger value for at least three consecutive readings followed by any continuous or monotonic decrease for at least three consecutive readings at any later point in time. Once these two conditions have occurred, a peak counter is incremented. The system continues looking for the next three increases followed by three decreases until the entire buffer has been examined, and the counter provides the number of peaks in the bottle signature.

Referring back to FIG. 5 which represents the digital signal of the BIG I bottle, it can be seen that there are two peaks in the signature as measured by sensor 12. The monotonic increases at a, b, c, and d are followed by monotonic decreases at e, f, and g thereby meeting the definition for a peak. The second peak is similar in nature.

AREA UNDER SIGNATURE FEATURE

The area feature is simply the sum of the integer values for all data points associated with a particular sensor (i.e., the total area under the curve). In the example of FIG. 5, the area for sensor 12 is 68 and the area for sensor 13 is 6.

SIGMA FEATURE

The sigma feature is the sum of the absolute values of the differences between consecutive integer data values for all the points associated with a particular sensor (i.e. absolute value of the sum of the vertical excursions). In the example of FIG. 5, the sigma feature is 40 for sensor 12 and 4 for sensor 13.

LARGEST GAP FEATURE

A gap is defined as the number of consecutive data points which are less than or equal to the integer 2 in the range of 0-31 (i.e., the length of the largest gap between peaks). The threshold value, 2 is an arbitrary design choice and may be changed if necessary.

RATIO FEATURE

The ratio feature value is the area feature value divided by the sigma feature value.

Figure 7:
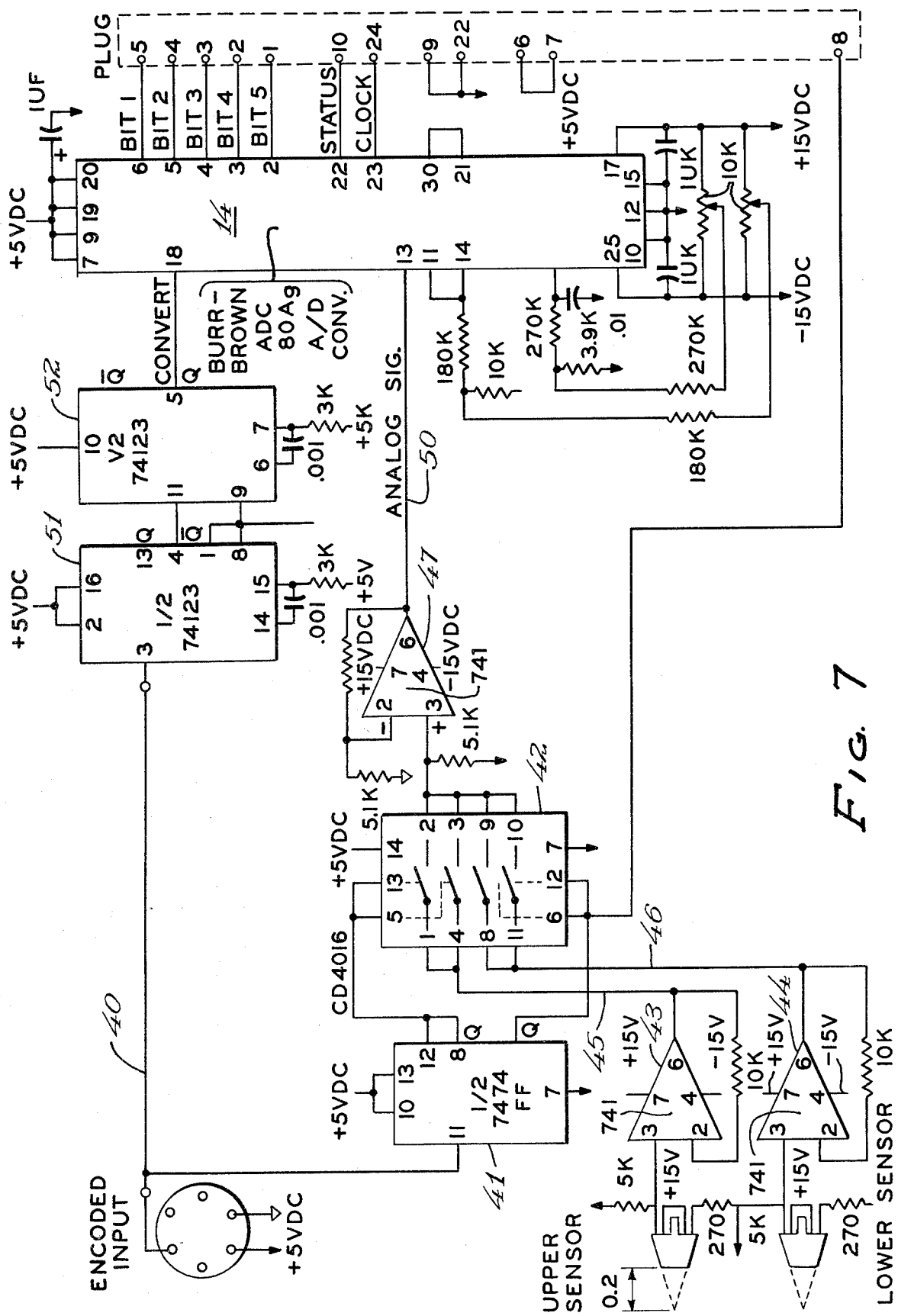
FIG. 7 is a schematic diagram of the electronic processing circuit.

FIG. 7 shows a schematic representation of an electronic interface for digitizing the signals received from the sensors. The signal from the shaft encoder 31 which is brought in on line 40, drives a flip-flop 41, such as a 7474, which in turn actuates an electronic switch 42, here shown as an RCA type CD4016. The analog signal from sensor 12 and the signal from sensor 13 are amplified by conventional 741 op. amps. 43 and 44, respectively, and connected by conductors 45 and 46 to the inputs of the switch 42. Switch 42 alternately passes the signal from sensor 12 and sensor 13, so that for each bottle rotation, the output consists of 256 pulses from sensor 13 interleaved with 256 pulses from sensor 12. The signals from switch 42 are amplified 47 and then are connected by conductor 50 into the analog-to-digital converter 14, such as Burr Brown type ADC80AG. The encoder signal on line 40 is also shaped by signal shapers 51 and 52 (type 74123) connected to the converter 14 and used as the convert command signal input to the A/D converter. The digitized output of converter 14 is brought out through a plug which provides proper input connections for the microcomputer.

Figure 8:
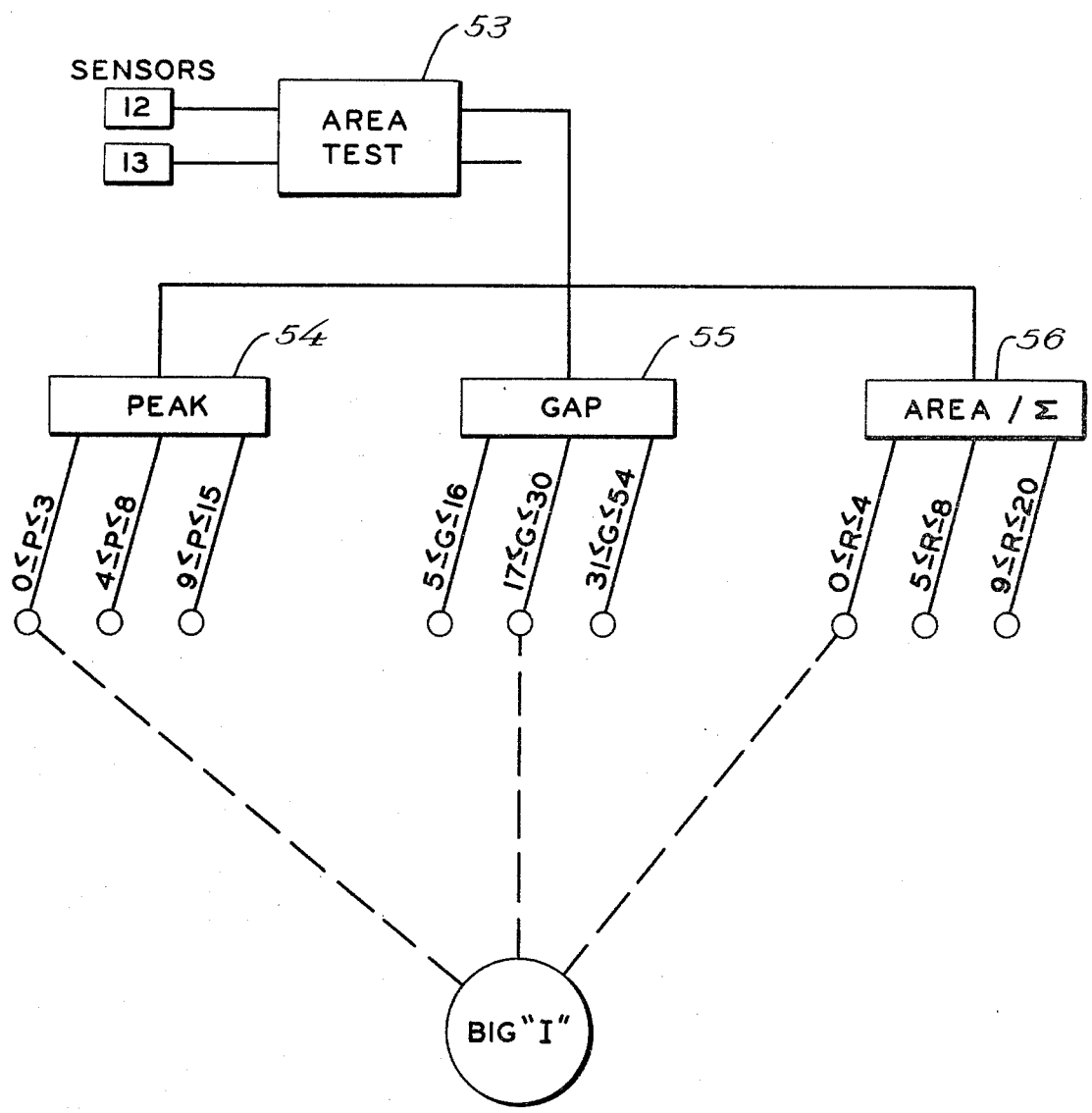
FIG. 8 shows an example of identifying a bottle of the type shown in the previous figures.

A simplified explanation of the way the signals are utilized in the microcomputer is shown diagramatically in FIG. 8. First the outputs from the two sensors are checked for the area; the one with the largest area (in this case #1) is picked and further analyzed. The sensor which is scanning a label or other identifying marks will generally have a much larger area under the signature with respect to the sensor which is just scanning bottle surface (no label) only. Therefore, the system's first consideration will be to select the sensor which is scanning the surface with valid identifying markings.

The next step consists of comparing the gap, peak count and ratio value with predetermined ranges and assigning a unique bit pattern to the range in which the value falls. This bit pattern is stored in the appropriate area of the ID word. The ID word is masked and modified to remove "don't care" states then compared with a known pattern to achieve bottle identification. Said another way, the number of peaks 54, longest gap 55 and the ratio of area to Σ 56 are computed, the ratio area/Σ is used in order to arrive at a "normalized" number, since both features are affected by the brightness of the graphics. These three features are then catagorized into groups, and the bottle identified by the combination. In the case of the BIG I bottle, the two peaks provide an output from the peak counter 54 on the $0 \leq p \leq 3$ output. The means 55 for determining the longest gap provides an output on the $17 \leq G \leq 30$ output; and the means 56 determining area divided by sigma provides an output at $0 \leq R \leq 4$. The BIG I bottle can thus be identified.

Figure 9:
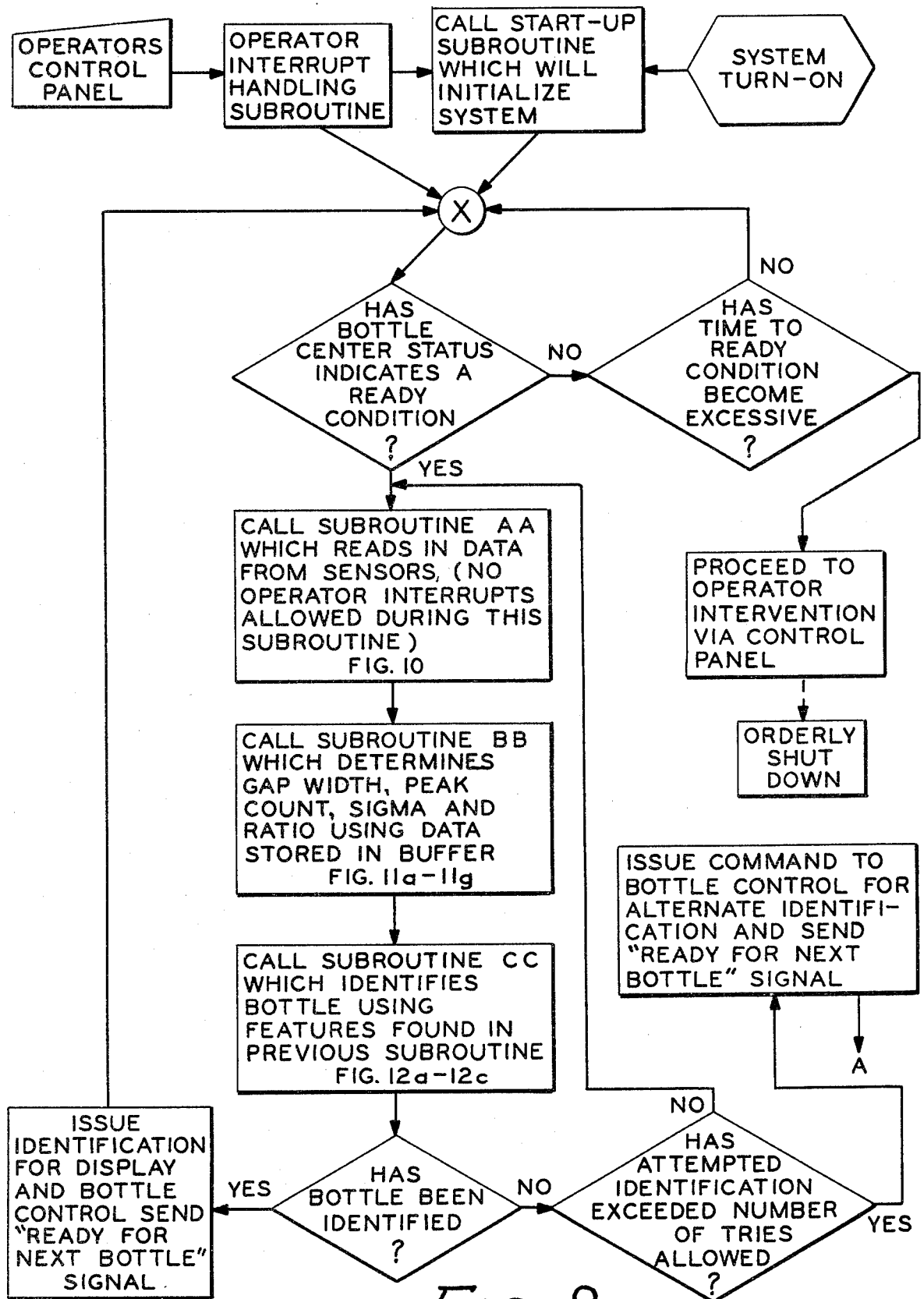
FIGS. 9-12C are flow charts.

Referring to FIGS. 9–12C, the flow diagram form of the computations performed in identifying the bottles is described. In FIG. 9, which shows a generalized flow, the program is entered through a system turn-on sequence and passes to the START-UP subroutine which initializes the system, the initialization procedure being known to those of ordinary skill in the microprocessor art and not being of significance in the invention. Following the START-UP control passes A to the BOTTLE CONTROL step where the determination is made has bottle control status indicated a ready condition. If not, the next step investigated is to determine whether the time to ready condition has become excessive, and if not the program returns to the BOTTLE CONTROL to test again. When the status indicates a ready condition, the program proceeds to call subroutine AA which reads in data from the sensors and stores the data in the buffer storage. Next the subroutine BB is called which determines the gap width, peak count, sigma, and the ratio of area/sigma using the data which was previously stored in the buffer. Then the subroutine CC is called which identifies the bottle, this by using the features found in the immediate preceding subroutine. The program then proceeds to inquire whether the bottle has been identified and if so proceeds to issue identification for display or bottle control and sends "ready for next bottle" signal.

Figure 10:
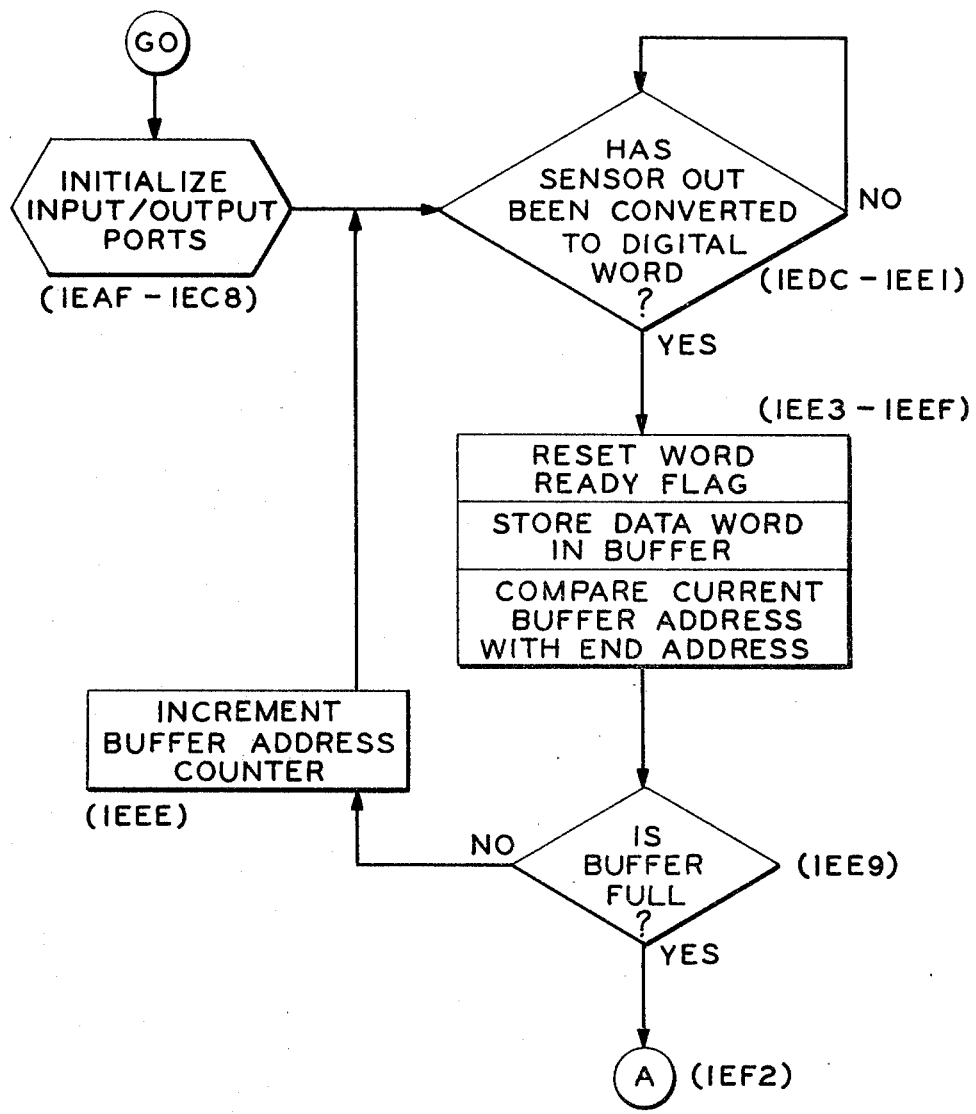

FIG. 10 is a flow diagram of the subroutine AA which reads in data from the sensors. When a GO signal is received the program proceeds to initialize the input-/output ports and then proceeds to test whether the sensor output has been converted to a digital word. If the test is yes the program proceeds to reset the word ready flag and to store the data word in the buffer and then to compare the current buffer address with the end address. The program then tests whether the buffer is full, if not the buffer address counter is incremented and the program returns to test for the next digital word. When the buffer is full, the subroutine ends and the subroutine BB is called up.

Figure 11A:
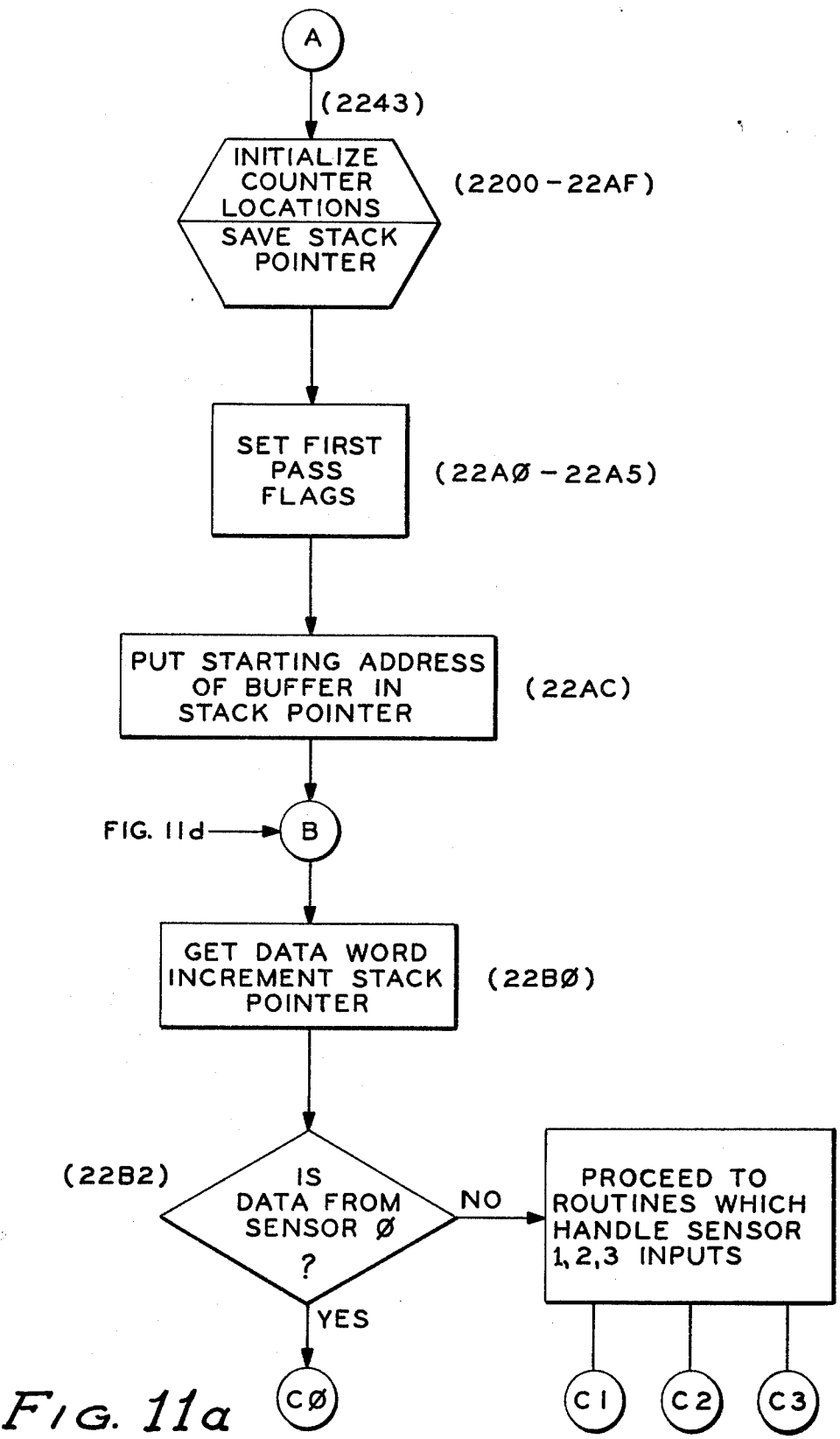
Figure 11B:
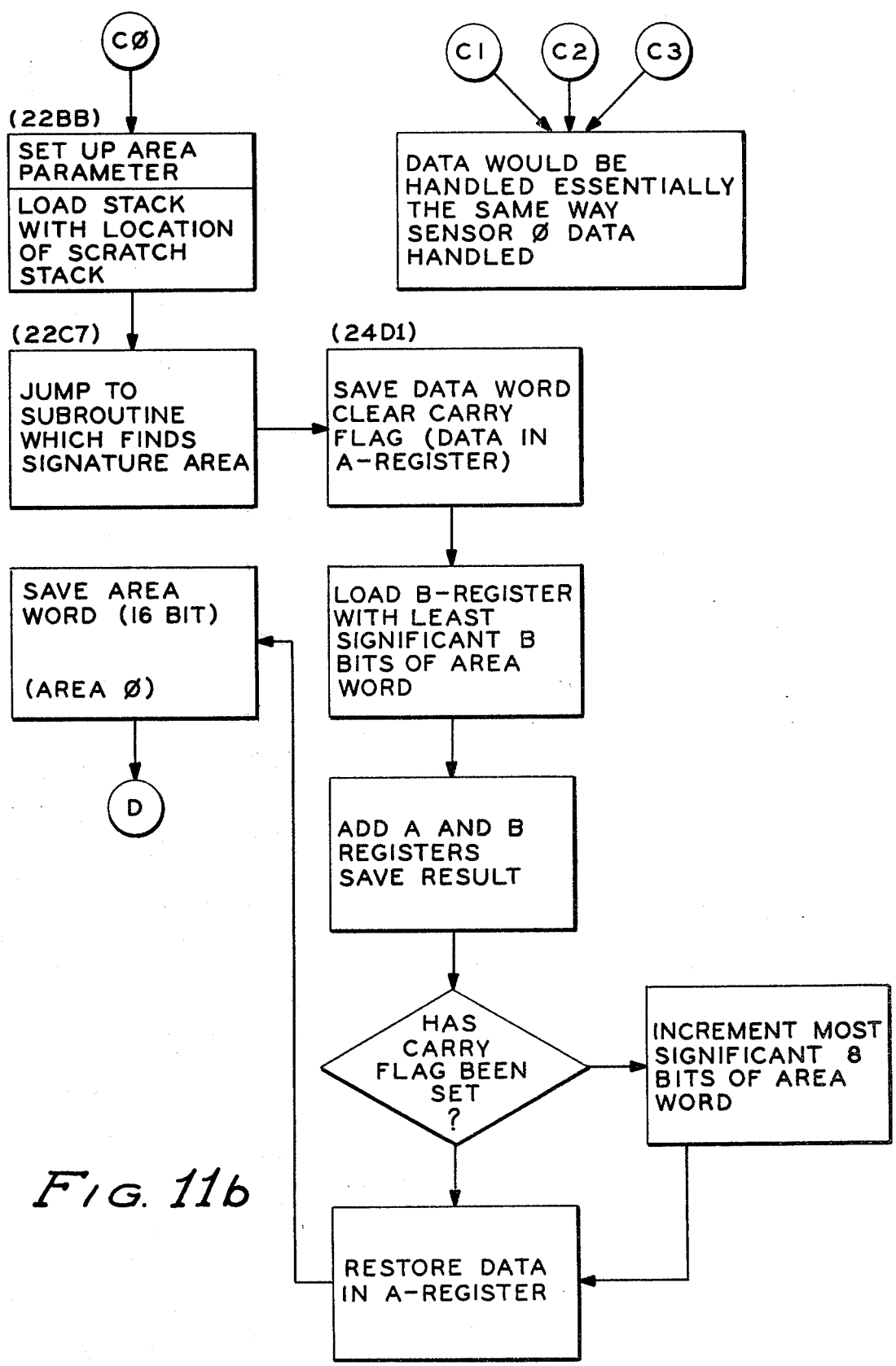

FIGS. 11a–11g show the flow diagram of the subroutine BB of FIG. 9, which manipulates the data in the buffer to obtain the "area" under the signature, the largest "gap" in the signature, "sigma" (summation of the absolute values of the differences between successive data values of signature), and the "number of peaks" in the signature. In FIG. 11a the subroutine is entered, the first step is to reset the counter locations. The stack pointer is saved thus preserving the address of the buffer stack. The first pass flag is then set and the program proceeds to put the starting address of the buffer in the stack pointer. The procedure advances on the flow diagram through point B and proceeds to get a data word. In the present description this may be the first word of the 512 stored in the buffer (or may be succeeding words triggered from the indicated FIG. 11d input of point B). In the process of retrieving the word, the stack pointer is also incremented to the next data word. The program then proceeds to test which sensor the data word is from. Continuing on FIG. 11b, the program proceeds to set up the area parameter by loading words into temporary locations which pass the values to be manipulated to the area subroutine. At this point in FIG. 11b the program jumps to an indicated subroutine which determines the signature area. First the data goes into the A-Register; the data word is saved and the program proceeds to clear the carry flag. Next the B-Register is loaded with the least significant 8 bits of the area word. The subroutine then adds the A and B registers and saves the result in the area word. Next the subroutine tests if the carry flag has been set, and if so, proceeds to increment the most significant 8-bit word in the 16-bit pair then saves the 16-bit area word. If the carry flag has not been set the original data is restored in the A-register. Now program flow returns out to the main program and saves the area word (16 bit).

Figure 11C:
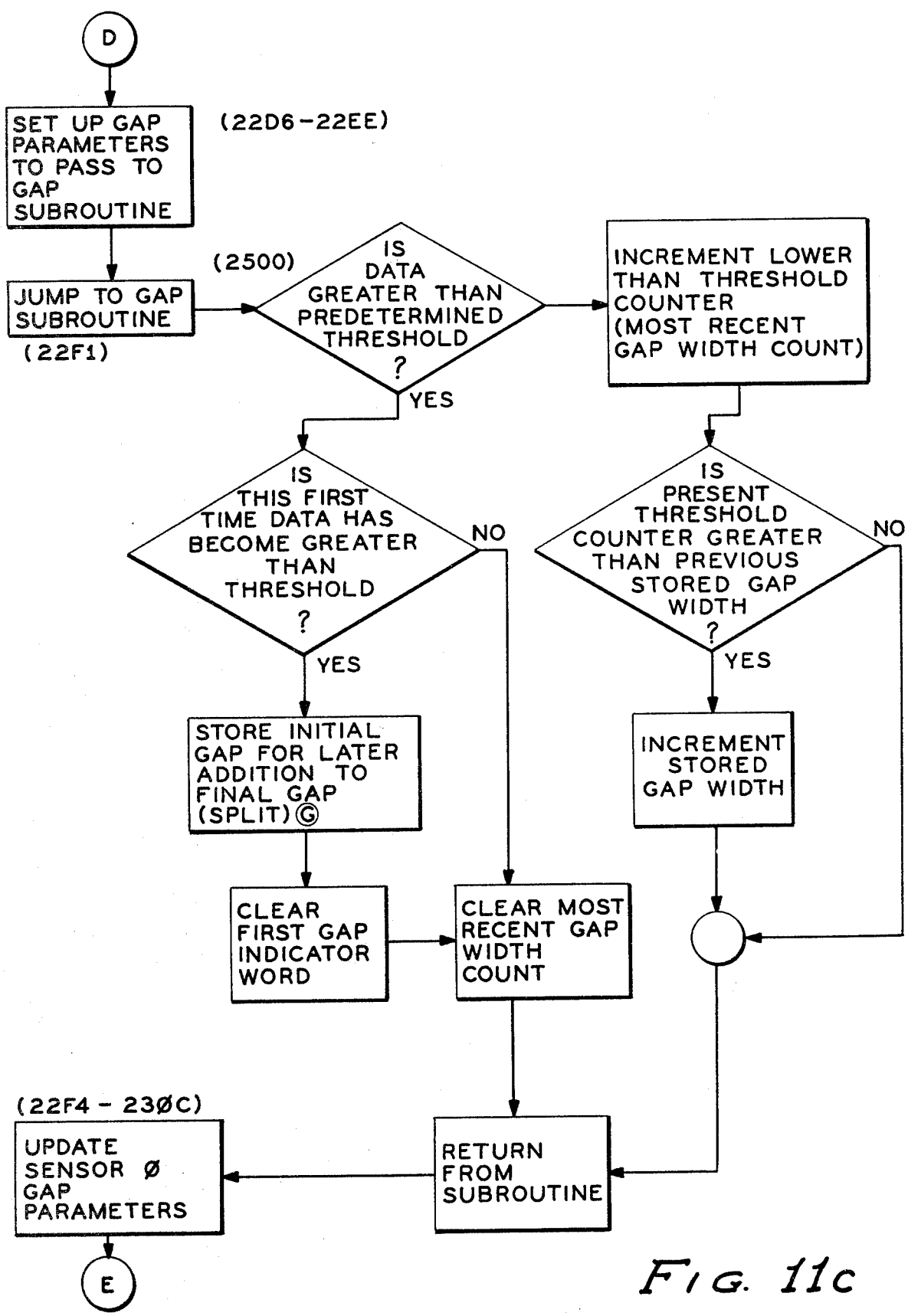

In FIG. 11c the program proceeds to set up the GAP parameters and jumps to the GAP routine. In the GAP subroutine the first test determines if the data is greater than a predetermined threshold. If not, the lower-than-threshold counter is incremented to provide the most recent gap width count. The next step is to determine if the present threshold counter is greater than that previously stored gap width. If not, return from subroutine, if yes, increment the stored gap width and return from subroutine. If the first test determines the data is greater than the threshold, the subroutine proceeds to determine if this is the first time the data has become greater than the threshold. If yes, the initial gap is stored for later addition to the final gap. The initial gap-final gap situation is also known as a split gap condition and occurs because the bottles are not indexed, but begin the rotation at a random point on the circumference of the bottle. Then the subroutine clears the first gap indicator word, to clear the most recent gap width count and returns from subroutine. If this is not the first time the data has become greater than the threshold, the subroutine clears the most recent gap width count and returns from subroutine. The program then proceeds to update the gap parameters.

Figure 11D:
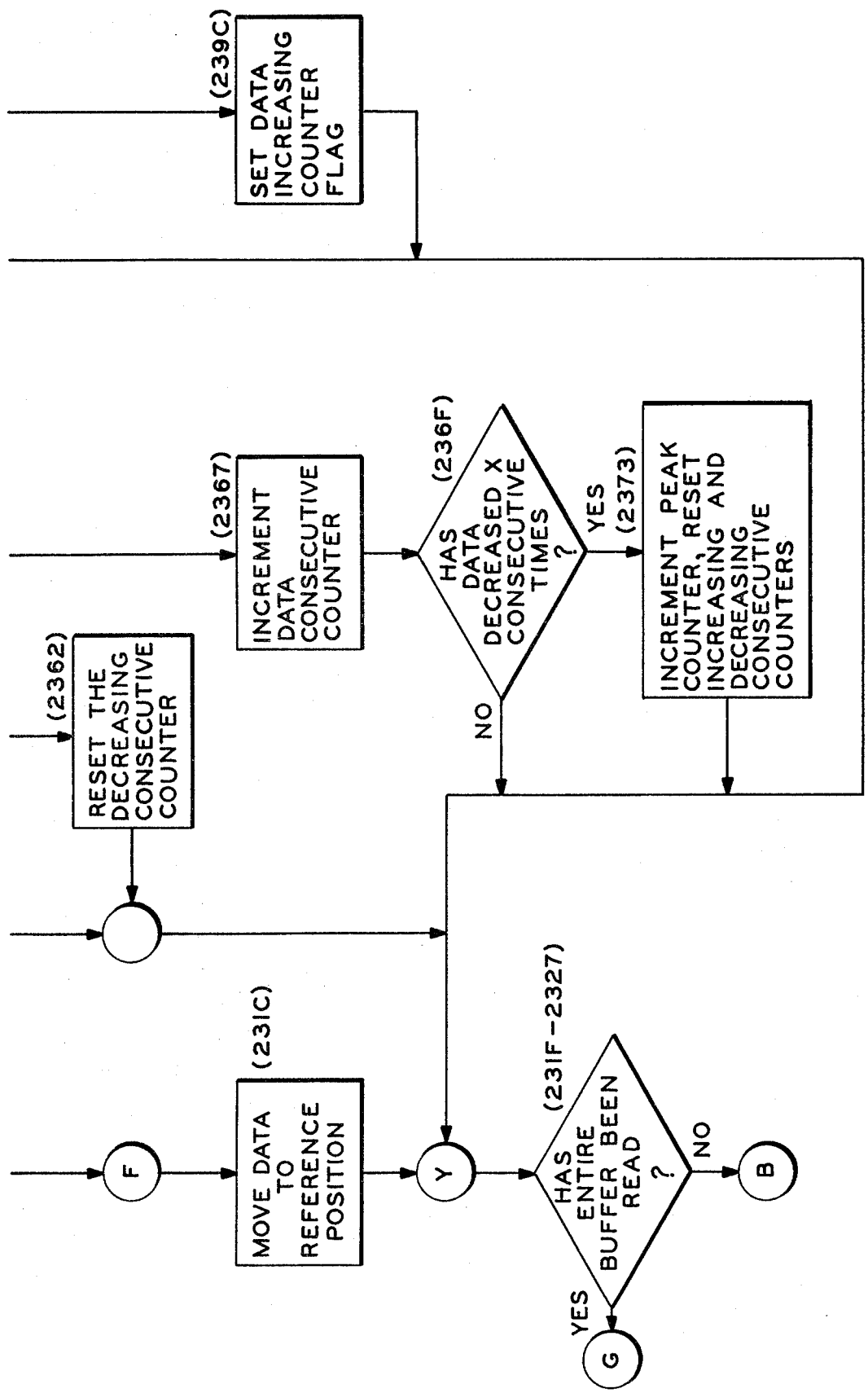
Figure 11E:
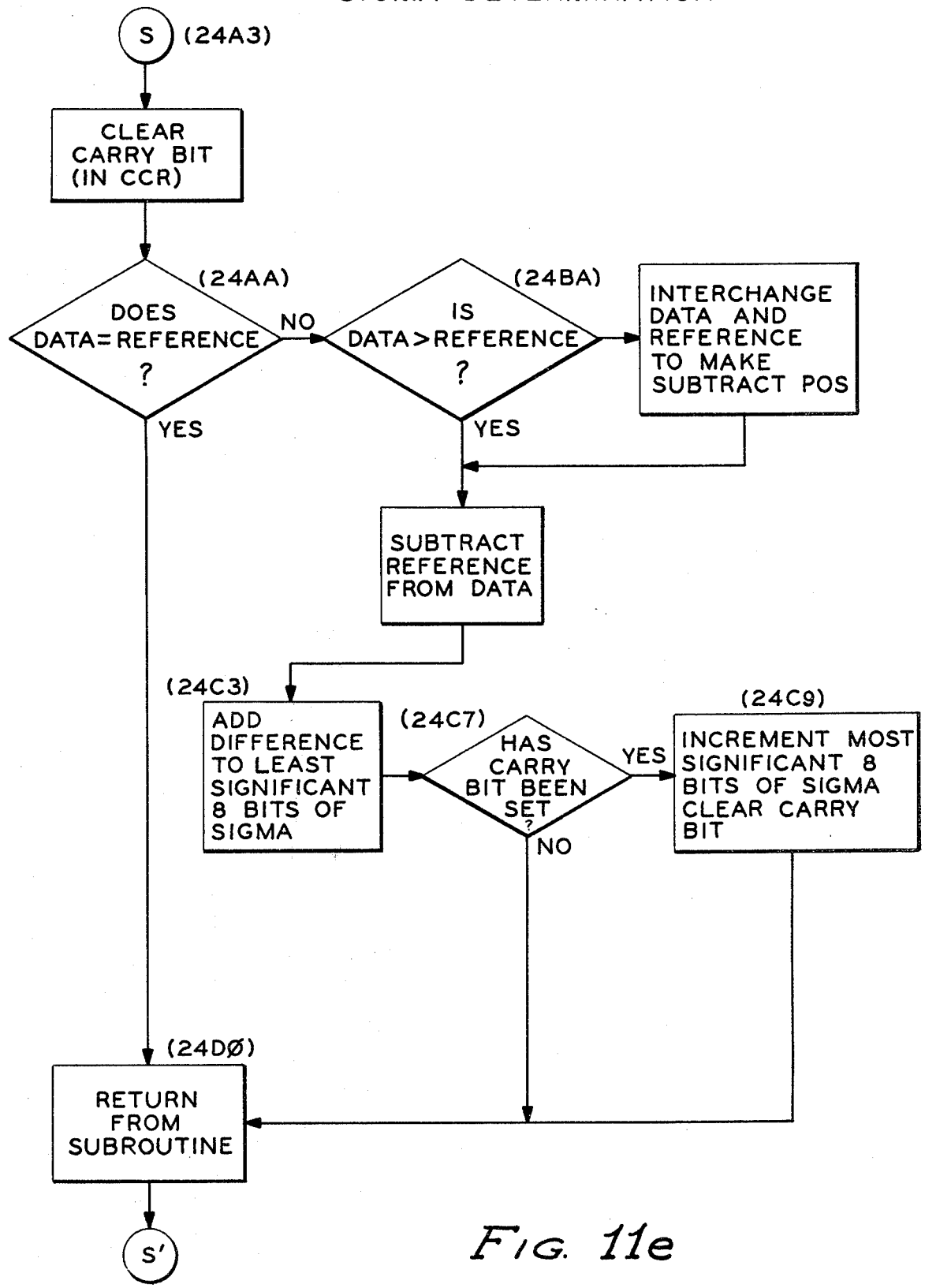

In FIG. 11d, the program first tests whether it is the first pass through the main program and if so, sets the first pass flag, proceeds to move the data to the reference position, passes junction Y and tests if entire buffer has been read. If entire buffer has not been read, go back to B, FIG. 11a. If on the second or successive pass, the next test determines if the data word equals the reference word. If it does not, there is a vertical excursion in the signal level which will provide an addition to the sigma total. Thus, if the data word does not equal the reference word, the next step is to save the data and the reference words, then to set up sigma parameters and jump to the sigma subroutine. Since the sigma determining subroutine is shown in FIG. 11e, a brief reference to that figure will be made before returning to the subroutine of FIG. 11d. In FIG. 11e, the first step is to clear the carry bit (in condition code register) followed by a test which determines if the data is equal to the reference. If not, a test is made to determine whether the data is greater than the reference. If it is, the next step is to subtract the reference from the data. If not, the data and reference are interchanged to make the result of the subtraction positive and then the subtraction is executed. In either case, the resulting difference from the subtraction step is added to the least significant 8 bits of sigma. Then the subroutine checks if the carry bit has been set. If no, return from subroutine to FIG. 11d. If yes, increment the most significant 8 bits of sigma, clear the carry bit and return from subroutine to FIG. 11d.

Back in the flow chart of FIG. 11d, the next step is to save the updated sigma values and to restore the data and reference if they were reversed above. The program then proceeds to determine if the data has increased X number of times. (3 was arbitrarily selected as X). If not, test if the data is greater than the reference. If so, increment the "data increasing counter" and check again if data has increased X consecutive times. If yes, set the "data increasing counter" flag and go to Y. If the data was not larger than the reference, then the "data increasing counter" is reset to zero and go to Y. If the program had determined earlier that the data had increased X number of times, then the next step is to determine if data is less than reference. If no, reset the "consecutive decreasing counter" and go to Y. If yes, increment the "consecutive decreasing counter" and determine if data has decreased X consecutive times, if not, go to Y. If yes, increment the peak counter to indicate another peak, reset the increasing and the decreasing consecutive counters and go to Y. When the entire buffer has been read, the output at the bottom of FIG. 11d is at G and the flow chart continues at FIG. 11f.

FIG. 11f shows the subroutine which adds the initial gap to the final gap if such a split gap situation exists. The first step is to clear the overflow bit flag. Then an addition step adds the count in the "lower-than-threshold-counter" to the split value obtained earlier and discussed in FIG. 11c. Then the subroutine proceeds to determine if the overflow bit has been set. If yes, the next step is to replace the gap width count with a count of 255 which indicates the gap is the entire bottle circumference, and then return from subroutine. If not, the next step determines if the previous addition sum is larger than the current gap width count. If not, return from subroutine; if yes, replace the gap count with the new value resulting from the addition and then return from subroutine.

Figure 11G:
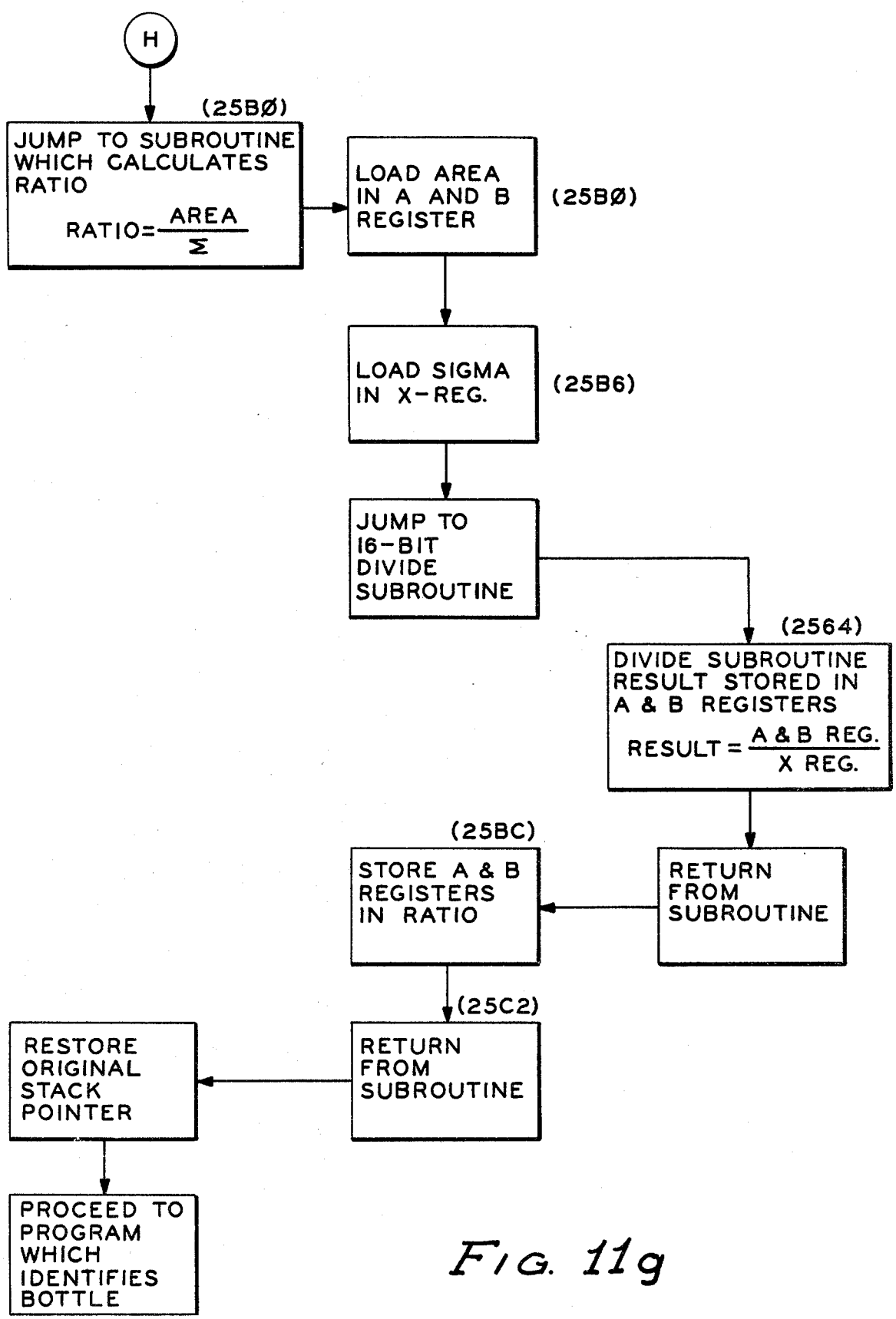

In FIG. 11g, the program continues entering at H and jumps to the subroutine which calculates the ratio between area and sigma. The area is loaded into the A and B registers (dividend), sigma is loaded into the X-register (divisor) and the division is performed. The ratio is stored in the A and B registers, the original stack pointer is restored and program flow advances to the program which identifies the bottle.

Figure 12A:
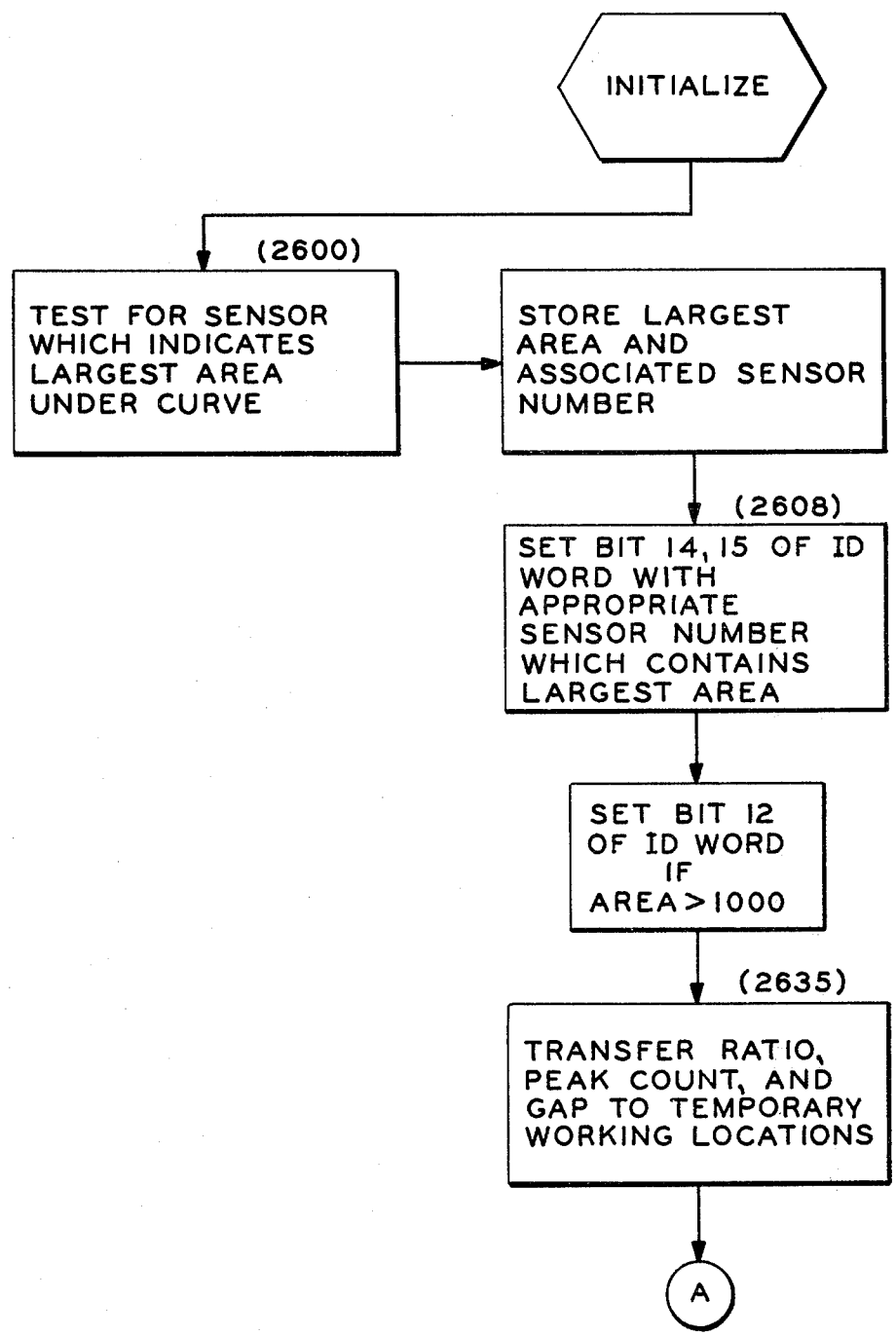
Figure 12B:
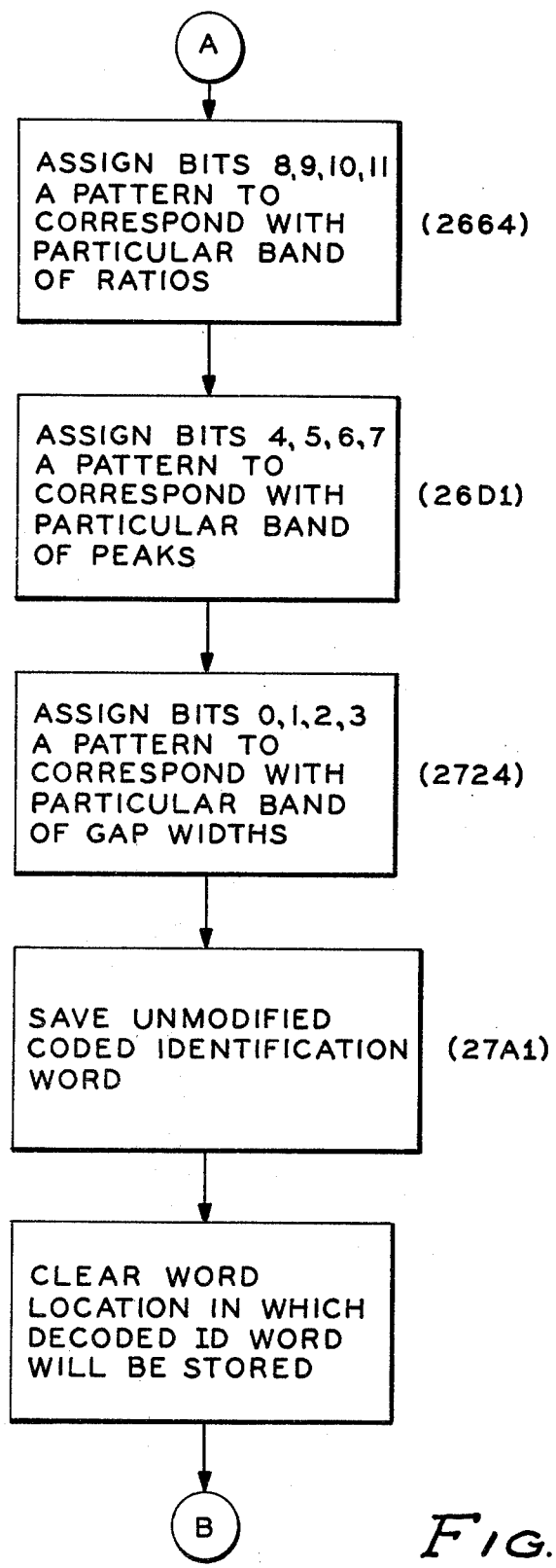
Figure 12C:
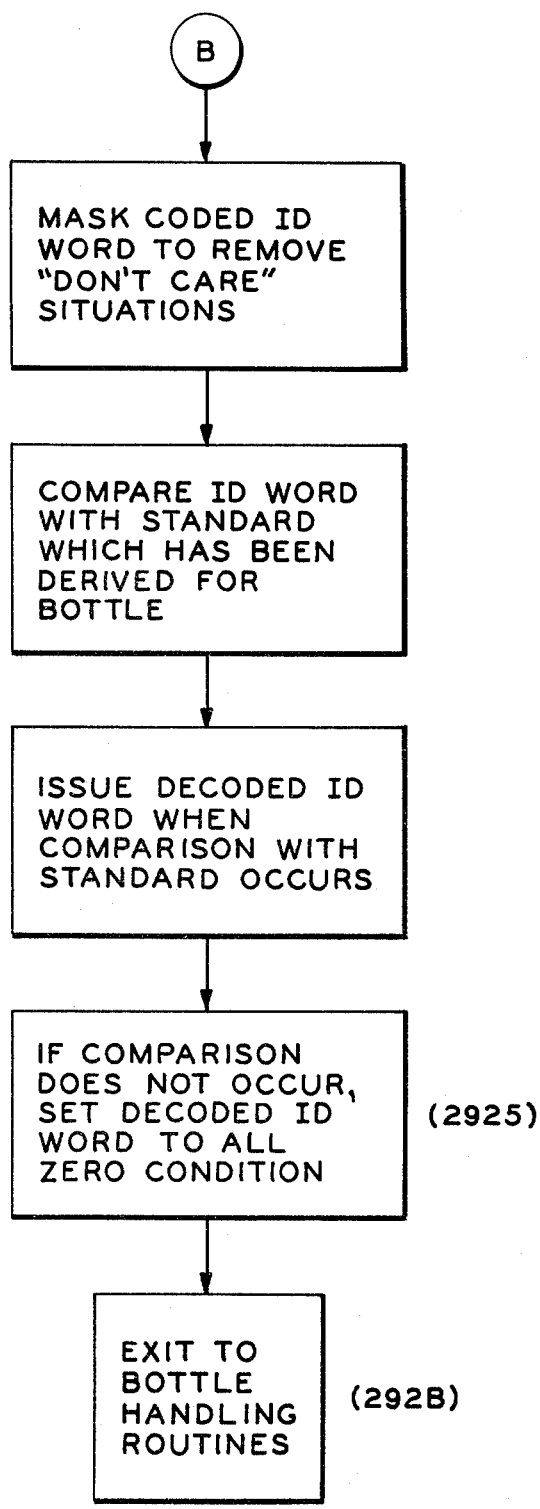

The flow diagram of FIGS. 12a, 12b and 12c describe in more detail the subroutine CC of FIG. 9 which identifies the bottle using features found in the previous subroutine. In FIG. 12a after initializing, the first test is to determine which sensor indicated the largest area under the curve, then the sensor number and the largest area is stored. The program then proceeds to set bit 14,15 of ID word with the appropriate sensor number and to set bit 12 of the ID word if the area is greater than a predetermined number. The program then proceeds to transfer the ratio, the peak count, and the gap to temporary working locations. Continuing on FIG. 12b, the program then proceeds to assign bits 8, 9, 10 and 11 a pattern to correspond with a particular band of ratios, to assign bits 4, 5, 6 and 7 a pattern to correspond with a particular band of peaks, and to assign bits 0, 1, 2 and 3 a pattern to correspond with a particular band of gap widths. The program then proceeds to save the unmodified coded ID word and to clear a word location into which the decoded ID word will be stored. In FIG. 12c, the coded word is then masked to remove "don't care" situations. The ID word is then compared with standard codes which have been derived for different types of bottles and when a comparison occurs to issue the decoded ID word. If a comparision does not occur, the program sets the decoded ID word to an all-zero condition. The program then exits to bottle handling.

In our design and testing up to the present time we have been able to identity 11 types of soft drink bottles using two sensors in the apparatus described. They are: COKE, SPRITE, FRESCA, TAB, 7-UP. DR. PEPPER, PEPSI, CRUSH, MASON'S, MOUNTAIN DEW, TOM MOORE, and in addition among these bottle types, three of them have two variations of graphics and two others have three variations of graphics. Sample signatures obtained from several types of bottles as they appear on an oscilloscope are shown in FIG. 13.

A program which is written in basic languages for directing the microprossessor operation to identify and sort bottles forms a portion of the description as set out in the following table.

```
00006         ;SUBROUTINE TO INPUT DATA FROM TWO SENSORS
00007         ;512 READINGS ARE STORED IN MEMORY LOCATIONS 1F00-20FF
00008         ;RANGE OF VALUES...0-31
00009         ;MEMORY LOCATIONS WITH MSB HIGH ARE SENSOR 1
00010         ;MEMORY LOCATIONS WITH MSB LOW ARE SENSOR 0
00011         ;STARTING ADDRESS...1EAF
00012         ;BASIC INTERPRETER MEMORY LOCATIONS 014E=22, 014F=00
00013         ;
00014         ;TO CALL USER FUNCTION...ENTER START ADDRESS IN 0067 AND 006
00015
00016         ; (IE POKE(103,30) AND POKE(104,175))

00018  8010   PDRA    EQU     8010H      ;PIA OUTPUT ADDRESS A
00019  8011   PCRA    EQU     8011H      ;PIA CONTROL REG A
00020  8012   PDRB    EQU     8012H      ;PIA INPUT ADDRESS B
00021  8013   PCRB    EQU     8013H      ;PIA CONTROL REG B
00022          ;
00023          ;ALLOW SPACE FOR DATA BUFFER
00024          ;
00025  1F00           ORG     1F00H
00026  1F00 0200 TABLE BLOCK   512
00027
00028          ;
00029          ;
```

```
00030                    ;START OF SUBR.
00031                    ;
00032                    ;
00033      1EAF                   ORG      1EAFH
00034                    ;
00035                    ;INITIALIZE PIA LINES AND REGISTERS
00036                    ;
00037 1EAF 8602  USER1   LDA A    #02
00038 1EB1 B78013         STA     A PCRB
00039 1EB4 4F             CLR     A
00040 1EB5 B78012         STA     A PDRB   ;ALL PB LINES ARE INPUT
00041 1EB8 8606           LDA     A #06    ;06=RISING EDGE, 04=FALLING EDGE
00042 1EBA B78013         STA     A PCRB   ;ALLOW READ ACCESS PB
00043                    ;
00044                    ;INITIALIZE OUTPUT LINES
00045                    ;
00046 1EBD 4F             CLR     A
00047 1EBE B78011         STA     A PCRA   ;SET UP OUTPUT DDR
00048 1EC1 86FF           LDA     A #0FFH
00049 1EC3 B78010         STA     A PDPA   ;ALL PA LINES ARE OUTPUT
00050 1EC6 8606           LDA     A #06    ;06=RISE, 04=FALL
00051 1EC8 B78011         STA     A PCRA   ;ALLOW WRITE ACCESS PA
00052                    ;
00053                    ;PIA LINES AND REGISTERS HAVE NOW BEEN INITIALIZED
00054                    ;
00055 1ECB CE1F00         LDX     #1F00H   ;512 WORD BUFFER START ADDRESS
00056 1ECE 5F             CLR     B
00057 1ECF F68010         LDA     B PDPA
00058 1ED2 F68011 NODIMP  LDA     B PCRA
00059 1ED5 2B02           BMI     DIMPHP
00060 1ED7 20F9           BRA     NODIMP
00061                    ;
00062                    ;
00063                    ;
00064 1ED9 B68012 DIMPHP  LDA     A PDRB   ;RESET HANDSHAKE FLAG
00065
00066                    ;
00067                    ;
00068                    ;LOOP TO WAIT FOR EDGE OF CB1 INDICATING DATA WORD READY
00069                    ;
00070                    ;
00071                    ;
00072 1EDC B68013 CHKFLG  LDA     A PCRB   ;FLAG IS BIT 7 OF CONTROL REG.
00073 1EDF 2B02           BMI     WDRDY
00074 1EE1 20F9           BRA     CHKFLG
00075                    ;
00076                    ;WHEN DATA READY,READ PERIPHERAL DATA REG AND STORE IN BUFFE
00077                    ;
00078 1EE3 B68012 WDRDY   LDA     A PDRB
00079 1EE6 43             COM     A        ;DATA FROM A->D IS INVERTED
00080 1EE7 A700           STA A   0,X
00081                    ;
00082                    ;CHECK IF BUFFER IS FULL
00083                    ;
00084 1EE9 8C20FF         CPX     #20FFH
00085 1EEC 2704           BEQ     ENDU1
00086 1EEE 08             INX              ;INC BUFF ADDR. CTR.
00087 1EEF 20EB           BRA     CHKFLG
00088 1EF1 01             NOP
00089 1EF2 39     ENDU1   RTS
00090      1EAF           END     USER1

00001                    ;        OVER0...SUBR WHICH ADDS SPLIT GAP
00002      2217  BGGAP0 EQU       2217H
00003      2218  BGGAP1 EQU       2218H
00004      222A  SPLIT0 EQU       222AH
00005      222B  SPLIT1 EQU       222BH
00006      221A  LTC0   EQU       221AH
00007      221B  LTC1   EQU       221BH
00008                    ;
00009      2530           ORG     2530H
00010                    ;
```

```
00011 2530 0A          OVER0   CLV
00012 2531 B6221A              LDA A    LTC0
00013 2534 BB222A              ADD A    SPLIT0
00014 2537 290A                BVS      OVER
00015 2539 B12217              CMP A    BGGAP0
00016 253C 230A                BLS      OVER1
00017 253E B72217              STA A    BGGAP0
00018 2541 2005                BRA      OVER1
00019 2543 86FF        OVER    LDA A    #0FFH
00020 2545 B72217              STA A    BGGAP0
00021 2548 0A          OVER1   CLV
00022 2549 B6221B              LDA A    LTC1
00023 254C BB222B              ADD A    SPLIT1
00024 254F 290A                BVS      OVER2
00025 2551 B12218              CMP A    BGGAP1
00026 2554 230A                BLS      THRU
00027 2556 B72218              STA A    BGGAP1
00028 2559 2005                BRA      THRU
00029 255B 86FF        OVER2   LDA A    #0FFH
00030 255D B72218              STA A    BGGAP1
00031 2560 39          THRU    RTS
00032      2530                END      OVER0

00001                          ;   GAP...SUBR WHICH FINDS LARGEST GAP
00002                          ;   BETWEEN BOTTLE LABELS
00003                          ;
00004      2219        LTC     EQU      2219H
00005      2216        TMGAP   EQU      2216H
00006      222C        FIRST   EQU      222CH
00007      2229        SPLIT   EQU      2229H
00008      2500                ORG      2500H
00009 2500 8102        GAP     CMP A    #02
00010 2502 2212                BHI      DGTT
00011 2504 7C2219              INC      LTC
00012 2507 F62219              LDA B    LTC
00013 250A F12216              CMP B    TMGAP
00014 250D 2202                BHI      GAP1
00015 250F 2016                BRA      GAPOUT
00016 2511 7C2216      GAP1    INC      TMGAP
00017 2514 2011                BRA      GAPOUT
00018 2516 F6222C      DGTT    LDA B    FIRST
00019 2519 2709                BEQ      DGTT1
00020 251B F62216              LDA B    TMGAP
00021 251E F72229              STA B    SPLIT
00022 2521 7F222C              CLR      FIRST
00023 2524 7F2219      DGTT1   CLR      LTC
00024 2527 39          GAPOUT  RTS

00001                          ;   RATO...SUBR.WHICH DIVIDES THE AREA BY
00002                          ;   SIGMA AND GIVES RATIO.
00003      2212        AREA0   EQU      2212H
00004      220C        SIGAD0  EQU      220CH
00005      2564        DIV16   EQU      2564H
00006      2233        RATIO0  EQU      2233H
00007                          ;
00008      25B0                ORG      25B0H
00009                          ;
00010 25B0 B62212      RATO    LDA A    AREA0
00011 25B3 F62213              LDA B    AREA0+1
00012 25B6 CE220C              LDX      #SIGAD0
00013 25B9 BD2564              JSR      DIV16
00014 25BC F72234              STA B    RATIO0+1
00015 25BF B72233              STA A    RATIO0
00016 25C2 39                  RTS

00001                          ;   DIVIDE...SUBROUTINE
00002                          ;   16 BIT UNSIGNED DIVIDE (16 BIT RESULT)
00003                          ;   A,B DIVIDED BY (X),(X+1)
00004                          ;   RESULT IN A,B   (X),(X+1) UNCHANGED
00005      2564                ORG      2564H
00006                          ;
00007 2564 37          DIV16   PSH B
00008 2565 36                  PSH A
00009                                            ;DIVIDEND NOW IN STACK
00010 2566 A600                LDA A    X
00011 2568 E601                LDA B    1,X
00012 256A 37                  PSH B
00013 256B 36                  PSH A
```

```
00014                                           ;DIVISOR NOW IN STACK
00015 256C 34                   DES             ;MAKE ROOM FOR COUNT
00016 256D 30                   TSX             ;(X) POINTER TO STACKED DATA
00017                        ;
00018 256E 8601                 LDA A   #01H
00019 2570 6D01                 TST     1,X
00020 2572 2D0B                 BMI     DIV153
00021                        ;
00022 2574 4C          DIV151  INC A
00023 2575 6802                 ASL     2,X
00024 2577 6901                 ROL     1,X
00025 2579 2B04                 BMI     DIV153
00026 257B 8117                 CMP A   #17H
00027 257D 26F5                 BNE     DIV151
00028                        ;
00029 257F A700        DIV153  STA A   0,X     ;SAVE COUNT
00030 2581 A603                 LDA A   3,X
00031 2583 E604                 LDA B   4,X
00032 2585 6F03                 CLR     3,X
00033 2587 6F04                 CLR     4,X
00034                        ;
00035 2589 E002        DIV163  SUB B   2,X
00036 258B A201                 SBC A   1,X
00037 258D 2407                 BCC     DIV165
00038 258F EB02                 ADD B   2,X
00039 2591 A901                 ADC A   1,X
00040 2593 0C                   CLC
00041 2594 2001                 BRA     DIV167
00042                        ;
00043 2596 0D          DIV165  SEC
00044                                           ;
00045 2597 6904        DIV167  ROL     4,X
00046 2599 6903                 ROL     3,X
00047 259B 6401                 LSR     1,X     ;ADJUST DIVISOR
00048 259D 6602                 ROR     2,X
00049 259F 6A00                 DEC     0,X
00050 25A1 26E6                 BNE     DIV163
00051                        ;CLEAN UP STACK
00052 25A3 31                   INS
00053 25A4 31                   INS
00054 25A5 31                   INS
00055 25A6 32                   PUL A
00056                                           ;
00057 25A7 33                   PUL B
00058 25A8 39                   RTS

00001                        ; THIS PROGRAM WILL COUNT PEAKS (DEFINED AS THREE
00002                        ; CONSECUTIVE INCREASES FOLLOWED BY THREE CONSECUTIVE DECREA
00003                        ; WILL SUM THE ABSOLUTE VALUES OF THE DIFFERENCES BETWEEN EA
00004                        ; DATA POINT, AND WILL CALCULATE THE AREA UNDER THE CURVE
00005                        ; OF THE DATA POINTS.
00006                        ;ALSO PROG.WILL DETERMINE LARGEST GAP BELOW FIXED THRESHOLD
00007                        ;
00008                        ;
00009       2200                 ORG     2200H
00010                        ;
00011 2200 01          PKCNT0  BYTE 1
00012 2201 01          PKCNT1  BYTE 1
00013 2202 0001        SAVSP   WORD    1
00014 2204 01          FLGWP   BYTE 1
00015 2205 01          FLGWN   BYTE 1
00016 2206 01          SCCP    BYTE 1
00017 2207 01          SCCN    BYTE 1
00018 2208 01          LCCP    BYTE 1
00019 2209 01          LCCN    BYTE 1
00020 220A 0001        SIGT    WORD    1
00021 220C 0001        SIG0    WORD    1
00022 220E 0001        SIG1    WORD    1
00023 2210 0001        AREAT   WORD    1
00024 2212 0001        AREA0   WORD    1
00025 2214 0001        AREA1   WORD    1
00026 2216 01          TMGAP   BYTE 1
00027 2217 01          BGGAP0  BYTE 1
00028 2218 01          BGGAP1  BYTE 1
```

```
00029 2219 01       LTC     BYTE  1
00030 221A 01       LTC0    BYTE  1
00031 221B 01       LTC1    BYTE  1
00032 221C 0001     BUFAD   WORD  1
00033 221E 0001     OLDSP   WORD  1
00034 2220 01       REFERP  BYTE  1
00035 2221 01       REFERN  BYTE  1
00036 2222 01       SIGREF  BYTE  1
00037 2223 01       SIGDAT  BYTE  1
00038 2224 0001     KEEPSP  WORD  1
00039 2226 01       SAVDAT  BYTE  1
00040 2227 0001     SSP     WORD  1
00041 2229 01       SPLIT   BYTE  1
00042 222A 01       SPLIT0  BYTE  1
00043 222B 01       SPLIT1  BYTE  1
00044 222C 01       FIRST   BYTE  1
00045 222D 01       FIRST0  BYTE  1
00046 222E 01       FIRST1  BYTE  1
00047 222F 0001     SIGAD0  WORD  1
00048 2231 0001     SIGAD1  WORD  1
00049 2233 0001     RATIO0  WORD  1
00050 2235 0001     RATIO1  WORD  1
00051 2237 01       RATIO   BYTE  1
00052 2238 01       PK      BYTE  1
00053 2239 0001     AMAX    WORD  1
00054 223B 01       IDMSW   BYTE  1
00055 223C 01       IDLSW   BYTE  1
00056 223D 01       IDWORD  BYTE  1
00057 223E 0001     ALTID   WORD  1
00058 2240 01       GAP0    BYTE  1
00059 2241 01       GAP1    BYTE  1
00060 2242 01       ZERP    BYTE  1
00061                       ;
00062                       ;
00063 2243 7F2200   PEKTST  CLR   PKCNT0
00064 2246 7F2201           CLR   PKCNT1
00065 2249 BF2202   SPSAV   STS   SAVSP
00066 224C 7F2205           CLR   FLGWN
00067 224F 7F2204           CLR   FLGWP
00068 2252 7F2207           CLR   SCCN
00069 2255 7F2206           CLR   SCCP
00070 2258 7F2209           CLR   LCCN
00071 225B 7F2208           CLR   LCCP
00072 225E 7F220A           CLR   SIGT
00073 2261 7F220B           CLR   SIGT+1
00074 2264 7F220C           CLR   SIG0
00075 2267 7F220D           CLR   SIG0+1
00076 226A 7F220E           CLR   SIG1
00077 226D 7F220F           CLR   SIG1+1
00078 2270 7F2212           CLR   AREA0
00079 2273 7F2213           CLR   AREA0+1
00080 2276 7F2214           CLR   AREA1
00081 2279 7F2215           CLR   AREA1+1
00082 227C 7F2210           CLR   AREAT
00083 227F 7F2211           CLR   AREAT+1
00084 2282 7F2216           CLR   TMGAP
00085 2285 7F2217           CLR   BGGAP0
00086 2288 7F2218           CLR   BGGAP1
00087 228B 7F2219           CLR   LTC
00088 228E 7F221A           CLR   LTC0
00089 2291 7F221B           CLR   LTC1
00090 2294 7F222A           CLR   SPLIT0
00091 2297 7F222B           CLR   SPLIT1
00092 229A 7F222D           CLR   FIRST0
00093 229D 7F222E           CLR   FIRST1
00094 22A0 73222D           COM   FIRST0
00095 22A3 73222E           COM   FIRST1
00096 22A6 CE1F00           LDX   #1F00H        ;BUFFER STARTING ADDRESS
00097 22A9 FF221C           STX   BUFAD
00098                       ;
00099 22AC BE221C           LDS   BUFAD         ;INITIALIZE STACK POINTER
00100 22AF 34               DES                 ;ADJUST SP FOR START OF BUFFER
00101                       ;
00102 22B0 32       PEAK    PUL A               ;GET DATA
00103 22B1 4D               TST A
00104 22B2 2B02             BMI   SEN1
00105 22B4 2005             BRA   SENS0
00106 22B6 847F     SEN1    AND A #7FH
```

```
00107 22B8 7E23A7            JMP    SENS1
00108                   ;
00109 22BB FE2212    SENS0  LDX    AREA0
00110 22BE FF2210           STX    AREAT
00111 22C1 BF221E           STS    OLDSP
00112 22C4 8E2F00           LDS    #2F00H
00113                  ;JUMP TO SUBR. WHICH FINDS AREA
00114                  ;
00115 22C7 BD24D1           JSR    AREA
00116                  ;
00117 22CA FE2210           LDX    AREAT
00118 22CD FF2212           STX    AREA0
00119 22D0 BE221E           LDS    OLDSP
00120                  ;
00121 22D3 BF221E           STS    OLDSP
00122 22D6 8E2F00           LDS    #2F00H
00123 22D9 F62217           LDA B  BGGAP0
00124 22DC F72216           STA B  TMGAP
00125 22DF F6221A           LDA B  LTC0
00126 22E2 F72219           STA B  LTC
00127 22E5 F6222D           LDA B  FIRST0
00128 22E8 F7222C           STA B  FIRST
00129 22EB F6222A           LDA B  SPLIT0
00130 22EE F72229           STA B  SPLIT
00131      2500     GAP    EQU    2500H
00132                  ;JUMP TO SUBROUTINE WHICH FINDS LARGEST GAP
00133 22F1 BD2500           JSR    GAP
00134                  ;
00135 22F4 BE221E           LDS    OLDSP
00136 22F7 F62216           LDA B  TMGAP
00137 22FA F72217           STA B  BGGAP0
00138 22FD F62219           LDA B  LTC
00139 2300 F7221A           STA B  LTC0
00140                  ;
00141 2303 F62229           LDA B  SPLIT
00142 2306 F7222A           STA B  SPLIT0
00143 2309 F6222C           LDA B  FIRST
00144 230C F7222D           STA B  FIRST0
00145                  ;
00146 230F C601             LDA B  #01H     ;CHECK FOR FIRST PASS
00147 2311 F52204            BIT B  FLGWP   ;B ANDED WITH FLAG WORD
00148 2314 2614             BNE    NOTFP    ;BRANCH IF NOT FIRST PASS
00149                  ;
00150 2316 FA2204    FPP    ORA B  FLGWP
00151 2319 F72204           STA B  FLGWP    ;SET FIRST PASS FLAG
00152                  ;
00153 231C B72220    POSREF STA A  REFERP   ;MOVE DATA TO REFERENCE
00154                  ;
00155 231F 30        DATEOP TSX
00156 2320 8C2101           CPX    #2101H   ;CHECK IF ALL DATA POINTS READ
00157 2323 2A02             BPL    FIN
00158 2325 2089             BRA    PEAK
00159 2327 7E2414    FIN    JMP    FINISH
00160                  ;
00161
00162                  ;
00163                  ;
00164                  ;
00165 232A B12220    NOTFP  CMP A  REFERP   ;IS DATA=REFERENCE
00166 232D 27F0             BEQ    DATEOP
00167 232F F62220           LDA B  REFERP
00168 2332 F72222           STA B  SIGREF
00169 2335 B72223           STA A  SIGDAT
00170 2338 B72226           STA A  SAVDAT
00171 233B FE220C           LDX    SIG0
00172 233E FF220A           STX    SIGT
00173 2341 BF2224           STS    KEEPSP
00174 2344 8E2F00           LDS    #2F00H
00175                  ;
00176                  ;JUMP TO SUBROUTINE WHICH CALCULATES SIGMA
00177                  ;
00178 2347 BD24A3           JSR    SIGMA
00179                  ;
00180 234A BE2224           LDS    KEEPSP
00181 234D FE220A           LDX    SIGT     ;GET TEMPORARY COUNT
00182 2350 FF220C           STX    SIG0     ;SAVE RUNNING SUM
00183 2353 B62226           LDA A  SAVDAT   ;RESTORE THE A-REGISTER
00184                  ;
```

```
00185 2356 C602                LDA B   #02
00186 2358 F52204              BIT B   FLGWP    ;TEST LCC FLAG
00187 235B 2729                BEQ     LCCNSP
00188                    ;
00189 235D B12220  LCCFSP      CMP A   REFERP
00190 2360 2305                BLS     DLTRP    ;BRANCH IF DATA<=REFER
00191 2362 7F2206              CLR     SCCP     ;RESET SCC GET ANOTHER DATA POINT
00192 2365 20B5                BRA     POSREF
00193                    ;
00194 2367 7C2206  DLTRP       INC     SCCP     ;COUNT INCREASE
00195 236A C602                LDA B   #02
00196 236C F12206              CMP B   SCCP
00197 236F 2702                BEQ     INCP0    ;BRANCHES IF SCC COUNT=2
00198 2371 20A9                BRA     POSREF
00199                    ;
00200 2373 7C2200  INCP0       INC     PKCNT0   ;COUNT PEAK
00201 2376 7F2206              CLR     SCCP     ;RESET COUNTERS AND FLAG
00202 2379 7F2208              CLR     LCCP
00203 237C C605                LDA B   #05
00204 237E F42204              AND B   FLGWP
00205 2381 F72204              STA B   FLGWP
00206 2384 2095                BRA     POSREF
00207                    ;
00208 2386 B12220  LCCNSP      CMP A   REFERP
00209 2389 2205                BHI     DGTRP    ;BRANCH IF DATA>REFER
00210 238B 7F2208              CLR     LCCP
00211 238E 208C                BRA     POSREF
00212                    ;
00213 2390 7C2208  DGTRP       INC     LCCP
00214 2393 C602                LDA B   #02
00215 2395 F12208              CMP B   LCCP     ;TEST FOR FULL COUNT
00216 2398 2702                BEQ     SLCCFP
00217 239A 2080                BRA     POSREF
00218                    ;
00219 239C C602    SLCCFP      LDA B   #02
00220 239E FA2204              ORA B   FLGWP
00221 23A1 F72204              STA B   FLGWP
00222 23A4 7E231C              JMP     POSREF
00223                    ;
00224 23A7 FE2214  SENS1       LDX     AREA1
00225 23AA FF2210              STX     AREAT
00226 23AD BF221E              STS     OLDSP
00227 23B0 8E2F00              LDS     #2F00H
00228            ;JUMP TO SUBR. WHICH DETERMINES AREA
00229                    ;
00230 23B3 BD24D1              JSR     AREA
00231                    ;
00232                    ;
00233 23B6 FE2210              LDX     AREAT
00234 23B9 FF2214              STX     AREA1
00235                    ;
00236 23BC BE221E              LDS     OLDSP
00237                    ;
00238 23BF BF221E              STS     OLDSP
00239 23C2 8E2F00              LDS     #2F00H
00240 23C5 F62218              LDA B   BGGAP1
00241 23C8 F72216              STA B   TMGAP
00242 23CB F6221B              LDA B   LTC1
00243 23CE F72219              STA B   LTC
00244 23D1 F6222E              LDA B   FIRST1
00245 23D4 F7222C              STA B   FIRST
00246 23D7 F6222B              LDA B   SPLIT1
00247 23DA F72229              STA B   SPLIT
00248            ;JUMP TO SUBROUTINE WHICH FINDS LARGEST GAP
00249 23DD BD2500              JSR     GAP
00250                    ;
00251 23E0 BE221E              LDS     OLDSP
00252 23E3 F62216              LDA B   TMGAP
00253 23E6 F72218              STA B   BGGAP1
00254 23E9 F62219              LDA B   LTC
00255 23EC F7221B              STA B   LTC1
00256 23EF F62229              LDA B   SPLIT
00257 23F2 F7222B              STA B   SPLIT1
00258 23F5 F6222C              LDA B   FIRST
00259 23F8 F7222E              STA B   FIRST1
00260                    ;
00261 23FB C601                LDA B   #01H     ;CHECK FOR FIRST PASS
```

```
00262 23FD F52205           BIT B   FLGWN   ;B ANDED WITH FLAG WORD
00263 2400 2622             BNE     NOTFN   ;BRANCH IF NOT FIRST PASS
00264           ;
00265 2402 FA2205    FPN    ORA B   FLGWN
00266 2405 F72205           STA B   FLGWN   ;SET FIRST PASS FLAG
00267           ;
00268 2408 B72221    NEGREF STA A   REFERN  ;MOVE DATA TO REFERENCE
00269           ;
00270 240B 30       DATEON  TSX
00271 240C 8C2101           CPX     #2101H  ;CHECK IF ALL DATA POINTS READ
00272 240F 2A03             BPL     FINISH
00273 2411 7E22B0           JMP     PEAK
00274      2530     OVER0   EQU     2530H
00275      25B0     RAT0    EQU     25B0H
00276      25D0     RAT1    EQU     25D0H
00277 2414 8E2F00   FINISH  LDS     #2F00H
00278           ;
00279 2417 BD2530           JSR     OVER0
00280 241A BD25B0           JSR     RAT0
00281 241D BD25D0           JSR     RAT1
00282           ;
00283
00284           ;
00285           ;
00286 2420 BE2202           LDS     SAVSP
00287 2423 39               RTS
00288           ;
00289 2424 B12221   NOTFN   CMP A   REFERN  ;IS DATA=REFERENCE
00290 2427 27E2             BEQ     DATEON
00291           ;
00292 2429 F62221           LDA B   REFERN
00293 242C F72222           STA B   SIGREF
00294 242F B72223           STA A   SIGDAT
00295 2432 B72226           STA A   SAVDAT
00296 2435 FE220E           LDX     SIG1
00297 2438 FF220A           STX     SIGT
00298 243B BF2224           STS     KEEPSP
00299 243E 8E2F00           LDS     #2F00H
00300           ;
00301           ;
00302 2441 BD24A3           JSR     SIGMA
00303           ;
00304 2444 BE2224           LDS     KEEPSP
00305 2447 FE220A           LDX     SIGT    ;GET TEMPORARY COUNT
00306 244A FF220E           STX     SIG1    ;SAVE RUNNING SUM
00307 244D B62226           LDA A   SAVDAT  ;RESTORE THE A-REGISTER
00308           ;
00309 2450 C602             LDA B   #02
00310 2452 F52205           BIT B   FLGWN   ;TEST LCC FLAG
00311 2455 2729             BEQ     LCCNSN
00312           ;
00313 2457 B12221   LCCFSN  CMP A   REFERN
00314 245A 2305             BLS     DLTRN   ;BRANCH IF DATA<=REFER
00315 245C 7F2207           CLR     SCCN    ;RESET SCC GET ANOTHER DATA POINT
00316 245F 20A7             BRA     NEGREF
00317           ;
00318 2461 7C2207   DLTRN   INC     SCCN    ;COUNT INCREASE
00319 2464 C602             LDA B   #02
00320 2466 F12207           CMP B   SCCN
00321 2469 2702             BEQ     INCP1   ;BRANCHES IF SCC COUNT=2
00322 246B 209B             BRA     NEGREF
00323           ;
00324 246D 7C2201   INCP1   INC     PKCNT1  ;COUNT PEAK
00325 2470 7F2207           CLR     SCCN    ;RESET COUNTERS AND FLAG
00326 2473 7F2209           CLR     LCCN
00327 2476 C605             LDA B   #05
00328 2478 F42205           AND B   FLGWN
00329 247B F72205           STA B   FLGWN
00330 247E 2088             BRA     NEGREF
00331           ;
00332 2480 B12221   LCCNSN  CMP A   REFERN
00333 2483 2206             BHI     DGTRN   ;BRANCH IF DATA>REFER
00334 2485 7F2209           CLR     LCCN
00335 2488 7E2408           JMP     NEGREF
00336           ;
00337 248B 7C2209   DGTRN   INC     LCCN
00338 248E C602             LDA B   #02
00339 2490 F12209           CMP B   LCCN    ;TEST FOR FULL COUNT
```

```
00340 2493 2703              BEQ     SLCCFN
00341 2495 7E2408             JMP    NEGREF
00342                  ;
00343 2498 C602    SLCCFN LDA B    #02
00344 249A FA2205             ORA B   FLGWN
00345 249D F72205             STA B   FLGWN
00346 24A0 7E2408             JMP     NEGREF
00347                  ;
00348                  ;
00349                  ;
00350                  ;
00351                  ; SUBROUTINE...SIGMA
00352                  ;
00353                  ;
00354                  ;
00355                  ;
00356                  ;
00357                  ;
00358 24A3 BF2227    SIGMA  STS     SSP
00359 24A6 0C                CLC
00360 24A7 B62223            LDA A   SIGDAT    ;GET DATA
00361 24AA B12222            CMP A   SIGREF    ; DOES DATA=REFERENCE
00362 24AD 271E              BEQ     SAME      ;BRANCH IF DATA=REFERENCE
00363 24AF 2209              BHI     DGTR      ;BRANCH IF DATA>REFERENCE
00364                  ;
00365 24B1 F62222    DLTR   LDA B   SIGREF
00366 24B4 F72223            STA B   SIGDAT
00367 24B7 B72222            STA A   SIGREF
00368                  ;
00369 24BA B62223    DGTR   LDA A   SIGDAT
00370 24BD B02222            SUB A   SIGREF
00371                  ;
00372 24C0 F6220B            LDA B   SIGT+1
00373 24C3 1B                ABA
00374 24C4 B7220B            STA A   SIGT+1
00375 24C7 2404              BCC     SAME
00376 24C9 7C220A            INC     SIGT
00377 24CC 0C                CLC
00378                  ;
00379 24CD BE2227    SAME   LDS     SSP
00380 24D0 39                RTS
00381                  ;AREA SUBROUTINE
00382                  ;
00383                  ;
00384                  ;
00385                  ;
00386 24D1 BF2227    AREA   STS     SSP       ;SAVE STACK POINTER
00387 24D4 B72226            STA A   SAVDAT
00388 24D7 0C                CLC
00389 24D9 F62211            LDA B   AREAT+1
00390 24DB 1B                ABA
00391 24DC B72211            STA A   AREAT+1
00392 24DF 2404              BCC     NOCARY
00393 24E1 7C2210            INC     AREAT
00394 24E4 0C                CLC
00395 24E5 BE2227    NOCARY LDS     SSP
00396 24E8 B62226            LDA A   SAVDAT
00397 24EB 39                RTS               ;RETURN TO MAIN PROG.
00001                  ; IDENT....SUBROUTINE WHICH IDENTIFIES BOTTLES
00002                  ; GIVEN PEAK COUNT, SIGMA, AREA, AND GAP WIDTH.
00003        2237     RATIO  EQU   2237H
00004        2238     PK     EQU   2238H
00005        2239     AMAX   EQU   2239H
00006        223B     IDMSW  EQU   223BH
00007        223C     IDLSW  EQU   223CH
00008        223D     IDWORD EQU   223DH
00009        223E     ALTID  EQU   223EH
00010        2240     GAP0   EQU   2240H
00011        2241     GAP1   EQU   2241H
00012        2242     GAP    EQU   2242H
00013        2212     AREA0  EQU   2212H
00014        2214     AREA1  EQU   2214H
00015        2233     RATIO0 EQU   2233H
00016        2235     RATIO1 EQU   2235H
00017        2200     PKCNT0 EQU   2200H
00018        2201     PKCNT1 EQU   2201H
00019        2217     BGGAP0 EQU   2217H
```

```
00020        2218        BGGAP1  EQU       2218H
00021                            ;
00022        2600                ORG       2600H
00023  2600  FE2212       IDENT  LDX       AREA0     ;TEST FOR LARGEST AREA
00024  2603  BC2214              CPX       AREA1
00025  2606  2B1F                BMI       IDENT1    ;BRANCH IF AREA1 LARGER
00026                            ;
00027  2608  8600                LDA  A    #00H
00028  260A  B7223C              STA  A    IDLSW
00029  260D  B7223B              STA  A    IDMSW
00030  2610  FF2239              STX       AMAX      ;AREA0 IS MAX
00031                            ;
00032  2613  B62234              LDA  A    RATIO0+1
00033  2616  B72237              STA  A    RATIO
00034  2619  B62200              LDA  A    PKCNT0
00035  261C  B72238              STA  A    PK
00036  261F  B62217              LDA  A    BGGAP0
00037  2622  B72242              STA  A    GAP
00038                            ;
00039  2625  2022                BRA       IDENT2    ;GO TO NEXT TEST
00040                            ;
00041  2627  8640         IDENT1 LDA  A    #40H      ;SET B14 OF IDWORD
00042  2629  B7223B              STA  A    IDMSW
00043  262C  8600                LDA  A    #00H
00044  262E  B7223C              STA  A    IDLSW
00045  2631  FE2214              LDX       AREA1
00046  2634  FF2239              STX       AMAX      ;USE ONLY MAX AREA FROM HERE ON
00047                            ;
00048  2637  B62236              LDA  A    RATIO1+1
00049  263A  B72237              STA  A    RATIO
00050  263D  B62201              LDA  A    PKCNT1
00051  2640  B72238              STA  A    PK
00052  2643  B62218              LDA  A    BGGAP1
00053  2646  B72242              STA  A    GAP
00054  2649  FE2239       IDENT2 LDX       AMAX
00055  264C  8C02FF              CPX       #2FFH
00056  264F  2A0A                BPL       IDENT3
00057                            ;
00058  2651  8600                LDA  A    #00H
00059  2653  BA223B              ORA  A    IDMSW
00060  2656  B7223B              STA  A    IDMSW
00061  2659  2008                BRA       IDENT4
00062                            ;
00063  265B  8610         IDENT3 LDA  A    #10H
00064  265D  BA223B              ORA  A    IDMSW
00065  2660  B7223B              STA  A    IDMSW
00066                            ;
00067  2663  B62237       IDENT4 LDA  A    RATIO
00068  2666  8105                CMP  A    #05H
00069  2668  2B22                BMI       RLT5
00070  266A  8108                CMP  A    #08H
00071  266C  2B28                BMI       RLT8
00072  266E  810B                CMP  A    #0BH
00073  2670  2B2E                BMI       RLT11
00074  2672  810D                CMP  A    #0DH
00075  2674  2B34                BMI       RLT13
00076  2676  810F                CMP  A    #0FH
00077  2678  2B3A                BMI       RLT15
00078  267A  8112                CMP  A    #12H
00079  267C  2B40                BMI       RLT18
00080  267E  8119                CMP  A    #19H
00081  2680  2B46                BMI       RLT25
00082                            ;
00083  2682  8608                LDA  A    #08H
00084  2684  BA223B              ORA  A    IDMSW
00085  2687  B7223B              STA  A    IDMSW
00086  268A  2044                BRA       IDENT5
00087  268C  86F0         RLT5   LDA  A    #0F0H
00088  268E  B4223B              AND  A    IDMSW
00089  2691  B7223B              STA  A    IDMSW
00090  2694  203A                BRA       IDENT5
00091                            ;
00092  2696  8601         RLT8   LDA  A    #01H
00093  2698  BA223B              ORA  A    IDMSW
00094  269B  B7223B              STA  A    IDMSW
00095  269E  2030                BRA       IDENT5
00096                            ;
```

```
00097 26A0 8603      RLT11   LDA A   #03H
00098 26A2 BA223B            ORA A   IDMSW
00099 26A5 B7223B            STA A   IDMSW
00100 26A8 2026             BRA     IDENT5
00101                   ;
00102 26AA 8607      RLT13   LDA A   #07H
00103 26AC BA223B            ORA A   IDMSW
00104 26AF B7223B            STA A   IDMSW
00105 26B2 201C             BRA     IDENT5
00106                   ;
00107 26B4 860F      RLT15   LDA A   #0FH
00108 26B6 BA223B            ORA A   IDMSW
00109 26B9 B7223B            STA A   IDMSW
00110 26BC 2012             BRA     IDENT5
00111                   ;
00112 26BE 860E      RLT18   LDA A   #0EH
00113 26C0 BA223B            ORA A   IDMSW
00114 26C3 B7223B            STA A   IDMSW
00115 26C6 2008             BRA     IDENT5
00116                   ;
00117 26C8 860C      RLT25   LDA A   #0CH
00118 26CA BA223B            ORA A   IDMSW
00119 26CD B7223B            STA A   IDMSW
00120                   ;
00121 26D0 B62238    IDENT5  LDA A   PK
00122 26D3 8103              CMP A   #03H
00123 26D5 2B1A              BMI     PLT3
00124 26D7 8106              CMP A   #06H
00125 26D9 2B20              BMI     PLT6
00126 26DB 8108              CMP A   #08H
00127 26DD 2B26              BMI     PLT8
00128 26DF 810B              CMP A   #0BH
00129 26E1 2B2C              BMI     PLT11
00130 26E3 8112              CMP A   #12H
00131 26E5 2B32              BMI     PLT18
00132                   ;
00133 26E7 86E0              LDA A   #0E0H
00134 26E9 BA223C            ORA A   IDLSW
00135 26EC B7223C            STA A   IDLSW
00136 26EF 2032              BRA     IDENT6
00137                   ;
00138 26F1 8600      PLT3    LDA A   #00H
00139 26F3 BA223C            ORA A   IDLSW
00140 26F6 B7223C            STA A   IDLSW
00141 26F9 2028              BRA     IDENT6
00142                   ;
00143 26FB 8610      PLT6    LDA A   #10H
00144 26FD BA223C            ORA A   IDLSW
00145 2700 B7223C            STA A   IDLSW
00146 2703 201E              BRA     IDENT6
00147                   ;
00148 2705 8630      PLT8    LDA A   #30H
00149 2707 BA223C            ORA A   IDLSW
00150                   ;
00151 270A B7223C            STA A   IDLSW
00152 270D 2014              BRA     IDENT6
00153                   ;
00154 270F 8670      PLT11   LDA A   #70H
00155 2711 BA223C            ORA A   IDLSW
00156 2714 B7223C            STA A   IDLSW
00157 2717 200A              BRA     IDENT6
00158                   ;
00159 2719 86F0      PLT18   LDA A   #0F0H
00160 271B BA223C            ORA A   IDLSW
00161 271E B7223C            STA A   IDLSW
00162 2721 2000              BRA     IDENT6
00163                   ;
00164 2723 B62242    IDENT6  LDA A   GAP
00165 2726 81FF              CMP A   #0FFH
00166 2728 2722              BEQ     GEQ255
00167 272A 8100              CMP A   #00H
00168 272C 2B6E              BMI     GLT254
00169 272E 8112              CMP A   #12H
00170 2730 2B24              BMI     GLT18
00171 2732 8117              CMP A   #17H
00172 2734 2B2A              BMI     GLT23
00173 2736 811E              CMP A   #1EH
```

```
00174 2738 2B30              BMI     GLT30
00175 273A 8128              CMP A   #28H
00176 273C 2B36              BMI     GLT40
00177 273E 8134              CMP A   #34H
00178 2740 2B3C              BMI     GLT52
00179 2742 813B              CMP A   #3BH
00180 2744 2B42              BMI     GLT59
00181 2746 814B              CMP A   #4BH
00182 2748 2B48              BMI     GLT75
00183 274A 2050              BRA     GLT254
00184                        ;
00185 274C 8609    GE0255    LDA A   #09H
00186 274E BA223C            ORA A   IDLSW
00187 2751 B7223C            STA A   IDLSW
00188 2754 2050              BRA     DONE
00189                        ;
00190 2756 8600    GLT18     LDA A   #0
00191 2758 BA223C            ORA A   IDLSW
00192 275B B7223C            STA A   IDLSW
00193 275E 2046              BRA     DONE
00194                        ;
00195 2760 8601    GLT23     LDA A   #01
00196 2762 BA223C            ORA A   IDLSW
00197 2765 B7223C            STA A   IDLSW
00198 2768 203C              BRA     DONE
00199                        ;
00200 276A 8603    GLT30     LDA A   #03
00201 276C BA223C            ORA A   IDLSW
00202 276F B7223C            STA A   IDLSW
00203 2772 2032              BRA     DONE
00204                        ;
00205 2774 8607    GLT40     LDA A   #07
00206 2776 BA223C            ORA A   IDLSW
00207 2779 B7223C            STA A   IDLSW
00208 277C 2028              BRA     DONE
00209                        ;
00210 277E 860F    GLT52     LDA A   #0FH
00211 2780 BA223C            ORA A   IDLSW
00212 2783 B7223C            STA A   IDLSW
00213 2786 201E              BRA     DONE
00214                        ;
00215 2788 860E    GLT59     LDA A   #0EH
00216 278A BA223C            ORA A   IDLSW
00217 278D B7223C            STA A   IDLSW
00218 2790 2014              BRA     DONE
00219                        ;
00220 2792 860C    GLT75     LDA A   #0CH
00221 2794 BA223C            ORA A   IDLSW
00222 2797 B7223C            STA A   IDLSW
00223 279A 200A              BRA     DONE
00224                        ;
00225 279C 8608    GLT254    LDA A   #08
00226 279E BA223C            ORA A   IDLSW
00227 27A1 B7223C            STA A   IDLSW
00228 27A4 2000              BRA     DONE
00229                        ;
00230 27A6 FE223B    DONE    LDX     IDMSW
00231 27A9 FF223E            STX     ALTID
00232 27AC 8600              LDA A   #0
00233 27AE B72915            STA A   IWORD2
00234 27B1 B7223D            STA A   IDWORD
00235 27B4 B6223B            LDA A   IDMSW
00236 27B7 84FF              AND A   #0FFH
00237 27B9 8151              CMP A   #51H
00238 27BB 2611              BNE     D1
00239 27BD B6223C            LDA A   IDLSW
00240 27C0 84FE              AND A   #0FEH
00241 27C2 81FE              CMP A   #0FEH
00242 27C4 2608              BNE     D1
00243 27C6 BA223D            ORA A   IDWORD
00244 27C9 8680    COKE      LDA A   #80H
00245 27CB B7223D            STA A   IDWORD
00246                        ;
00247 27CE B6223B    D1      LDA A   IDMSW
00248 27D1 84FB              AND A   #0FBH
00249 27D3 8158              CMP A   #58H
00250 27D5 2611              BNE     D2
```

```
00251 27D7 B6223C          LDA A   IDLSW
00252 27DA 84DD            AND A   #0DDH
00253 27DC 811C            CMP A   #1CH
00254 27DE 2608            BNE     D2
00255 27E0 8640   CRUSH    LDA A   #40H
00256 27E2 BA223D          ORA A   IDWORD
00257 27E5 B7223D          STA A   IDWORD
00258                  ;
00259                  ;
00260 27E8 B6223B   D2     LDA A   IDMSW
00261 27EB 84FD            AND A   #0FDH
00262 27ED 8111            CMP A   #11H
00263 27EF 2611            BNE     D3
00264 27F1 B6223C          LDA A   IDLSW
00265 27F4 849D            AND A   #9DH
00266 27F6 811C            CMP A   #1CH
00267 27F8 2608            BNE     D3
00268 27FA 8620   TABO     LDA A   #20H
00269 27FC BA223D          ORA A   IDWORD
00270 27FF B7223D          STA A   IDWORD
00271                  ;
00272                  ;
00273 2802 B6223B   D3     LDA A   IDMSW
00274 2805 84F7            AND A   #0F7H
00275 2807 8117            CMP A   #17H
00276 2809 2611            BNE     D4
00277 280B B6223C          LDA A   IDLSW
00278 280E 84FE            AND A   #0FEH
00279 2810 81F0            CMP A   #0F0H
00280 2812 2608            BNE     D4
00281 2814 8610   FRESCA   LDA A   #10H
00282 2816 BA223D          ORA A   IDWORD
00283 2819 B7223D          STA A   IDWORD
00284                  ;
00285                  ;
00286 281C B6223B   D4     LDA A   IDMSW
00287 281F 84FD            AND A   #0FDH
00288 2821 8111            CMP A   #11H
00289 2823 2611            BNE     D5
00290 2825 B6223C          LDA A   IDLSW
00291 2828 849B            AND A   #9BH
00292 282A 8113            CMP A   #13H
00293 282C 2608            BNE     D5
00294 282E 8608   SPRITE   LDA A   #08H
00295 2830 BA223D          ORA A   IDWORD
00296 2833 B7223D          STA A   IDWORD
00297                  ;
00298                  ;
00299 2836 B6223B   D5     LDA A   IDMSW
00300 2839 84F3            AND A   #0F3H
00301 283B 8113            CMP A   #13H
00302 283D 2611            BNE     D6
00303 283F B6223C          LDA A   IDLSW
00304 2842 84EF            AND A   #0EFH
00305 2844 8108            CMP A   #08H
00306 2846 2608            BNE     D6
00307 2848 8604   MOORE    LDA A   #04H
00308 284A BA223D          ORA A   IDWORD
00309 284D B7223D          STA A   IDWORD
00310                  ;
00311                  ;
00312 2850 B6223B   D6     LDA A   IDMSW
00313 2853 84FF            AND A   #0FFH
00314 2855 8113            CMP A   #13H
00315 2857 2609            BNE     D7
00316 2859 B6223C          LDA A   IDLSW
00317 285C 84FF            AND A   #0FFH
00318 285E 81F3            CMP A   #0F3H
00319 2860 2712            BEQ     MASONS
00320                  ;
00321 2862 B6223B   D7     LDA A   IDMSW
00322 2865 84FC            AND A   #0FCH
00323 2867 811C            CMP A   #1CH
00324 2869 2611            BNE     D8
00325 286B B6223C          LDA A   IDLSW
00326 286E 84FF            AND A   #0FFH
00327 2870 811C            CMP A   #1CH
```

```
00328 2872 2608              BNE         D8
00329 2874 8602     MASONS LDA A         #02H
00330 2876 BA223D           ORA A        IDWORD
00331 2879 B7223D           STA A        IDWORD
00332                    ;
00333                    ;
00334 287C B6223C    D8    LDA A         IDLSW
00335 287F 84F0            AND A         #0F0H
00336 2881 8100            CMP A         #00H
00337 2883 2611            BNE           D10
00338 2885 B6223C          LDA A         IDLSW
00339 2888 840F            AND A         #0FH
00340 288A 8109            CMP A         #09H
00341 288C 2708            BEQ           D10
00342 288E 8601    NFEAT   LDA A         #01H
00343 2890 BA223D          ORA A         IDWORD
00344 2893 B7223D          STA A         IDWORD
00345                    ;
00346                    ;
00347 2896 B6223B   D10    LDA A         IDMSW
00348 2899 84F0            AND A         #0F0H
00349 289B 8100            CMP A         #00H
00350 289D 2611            BNE           D11
00351 289F B6223C          LDA A         IDLSW
00352 28A2 84EF            AND A         #0EFH
00353 28A4 8108            CMP A         #08H
00354 28A6 2608            BNE           D11
00355 28A8 8680    P7M     LDA A         #80H
00356 28AA BA2915          ORA A         IWORD2
00357 28AD B72915          STA A         IWORD2
00358                    ;
00359 28B0 B6223B   D11    LDA A         IDMSW
00360 28B3 84E0            AND A         #0E0H
00361 28B5 8100            CMP A         #00H
00362 28B7 2611            BNE           D12
00363 28B9 B6223C          LDA A         IDLSW
00364 28BC 84FF            AND A         #0FFH
00365 28BE 811E            CMP A         #1EH
00366 28C0 2608            BNE           D12
00367 28C2 8640    FANTA   LDA A         #40H
00368 28C4 BA2915          ORA A         IWORD2
00369 28C7 B72915          STA A         IWORD2
00370                    ;
00371 28CA B6223B   D12    LDA A         IDMSW
00372 28CD 84EB            AND A         #0EBH
00373 28CF 8108            CMP A         #08H
00374 28D1 2611            BNE           D13
00375 28D3 B6223C          LDA A         IDLSW
00376 28D6 84FD            AND A         #0FDH
00377 28D8 810C            CMP A         #0CH
00378 28DA 2608            BNE           D13
00379 28DC 8620   PEPPER   LDA A         #20H
00380 28DE BA2915          ORA A         IWORD2
00381 28E1 B72915          STA A         IWORD2
00382                    ;
00383                    ;
00384 28E4 B6223B   D13    LDA A         IDMSW
00385 28E7 84B0            AND A         #0B0H
00386 28E9 8100            CMP A         #00H
00387 28EB 2611            BNE           D14
00388 28ED B6223C          LDA A         IDLSW
00389 28F0 840F            AND A         #0FH
00390 28F2 8109            CMP A         #09H
00391 28F4 2608            BNE           D14
00392 28F6 8610   NLABEL   LDA A         #10H
00393 28F8 BA2915          ORA A         IWORD2
00394 28FB B72915          STA A         IWORD2
00395                    ;
00396                    ;
00397 28FE B6223D   D14    LDA A         IDWORD
00398 2901 8100            CMP A         #00H
00399 2903 260F            BNE           D15
00400 2905 B62915          LDA A         IWORD2
00401 2908 8100            CMP A         #00H
00402 290A 2608            BNE           D15
00403 290C 8608    UNK     LDA A         #08H
00404 290E BA2915          ORA A         IWORD2
```

```
00405 2911 B72915            STA A    IWORD2
00406                        ;
00407                        ;
00408 2914 39                D15      RTS
00409 2915 01                IWORD2   BYTE     1
00410                        ;
00411                        ;
```

The embodiments of the invention in which an exclusive property or right is claimed are defined as follows:

1. Pattern recognition apparatus comprising:
   optical sensor means detecting reflected light from the surface of goods having a pattern to be identified, the sensor means scanning a line across the goods as the goods pass in front of the sensor means, the light reflected from the pattern of the passing goods providing an analog signal pattern output from said sensing means which analog signal pattern is characteristic of the pattern sensed;
   means for sampling the analog signal pattern at predetermined increments of movement of the goods and means converting each said signal sample to a digital bit;
   means for temporarily storing the digital bits representing the signal pattern from said goods, said temporarily stored digital signal containing information which can be expressed as signal peaks, area under the curve of the digital signal, gap in the signal, and vertical excursions of the digital signal from one bit to the next;
   means for counting the number of peaks of the digital signal;
   means for determining the area under the curve of the digital signal;
   means for determining the largest gap in the digital signal, where gap is defined as the number of consecutive data points at a signal level of less than a predetermined digital number;
   means for summing the total of the positive and negative vertical excursions of the digital signal, the sum being referred to as sigma;
   means for dividing the area value by the sigma value to obtain a value Y; and,
   means for comparing the number of peaks, the area, the largest gap, and the value Y with prestored information characteristic of each pattern type to be recognized.

2. Bottle identifying apparatus comprising:
   means for rotating a bottle to be identified;
   optical sensor means detecting reflected light from the surface of a bottle to be identified, the sensor means scanning a line across the graphics of the bottle as the bottle rotates in front of the sensor means, the light reflected from the rotating bottle graphics during a rotation of the bottle providing an analog signal pattern output from said sensing means which analog signal pattern is characteristic of that bottle type;
   means for sampling the analog signal pattern at angular increments of 360°/x during the rotation of the bottle and means converting each signal sample to a digital bit where x is an integer;
   means for temporarily storing the x digital bits representing the signal pattern from a rotation of said bottle, said temporarily stored digital signal containing information which can be expressed as signal peaks, area under the curve of the data points of the signal, gap in the signal, and vertical excursions of the digital signal from one bit to the next;
   means for counting the number of peaks of the digital signal;
   means for determining the area under the curve of the digital signal;
   means for determining the largest gap in the digital signal, where gap is defined as the number of consecutive data points at a signal level of less than a predetermined digital number;
   means for summing the total of the positive and negative vertical excursions of the digital signal, the sum being referred to as sigma;
   means for dividing the area value by the sigma value to obtain a value Y; and,
   means for comparing the number of peaks, the area, the largest gap, and the value Y with prestored information characteristic of each bottle type to be recognized.

3. Bottle identifying apparatus, comprising:
   first and second optical sensor means;
   means for rotating a bottle to be identified, said first and second optical sensor means each being mounted in proximity to the rotating bottle and each illuminating an area of and receiving reflective light from bottle graphics in the illuminated area of the rotating bottle, the sensor means each providing an analog electrical output signal proportional to the reflected light from the bottle surface as the bottle rotates;
   shaft encoder means connected to said bottle rotating means, said shaft encoder means providing a predetermined number of output electrical pulses during a rotation of the bottle;
   means including switching means actuated in response to the shaft encoder pulses and selectively connecting said first and second sensor means output sigma to analog-to-digital converter means at each occurrence of said shaft encoder means;
   analog-to-digital converter means actuated in response to the shaft encoder pulses having an input circuit adapted to be connected to receive said analog signals and to convert said signals to a digital form;
   means connecting said shaft encoder output pulses to said converter means to initiate the analog-to-digital conversion at the occurrence of each said pulse;
   permanent storage means for storing digital information characteristic of each bottle type to be recognized;
   memory means for temporarily storing the digital bits representing the two signal patterns from a rotation of said bottle, said temporarily stored digital signals containing information which can be expressed as signal peaks, area under the curve of the digital signal, gap in the signal, and vertical excursions of the digital signal from one bit to the next;
   means for determining the area under the curve of the digital signal;
   means for counting the number of peaks of the digital signal;
   means for determining the largest gap in the digital signal, where gap is defined as the number of consecutive data points at a signal level of less than a predetermined digital number;
   means for summing the total of the positive and negative vertical excursions of the digital signal, the sum being referred to as sigma;
   means for dividing the area value by the signal value to obtain a value Y; and, means for comparing said number of peaks, said area under the curve, said largest gap, and the value Y with prestored information as to peaks, area, gap and Y characteristic of each bottle type to be recognized.

4. The apparatus of claim 3 wherein said means for comparing further comprises means for checking the digital signal outputs of the two sensors for the area under the curve of each and for selecting the signal of larger area for further analysis.

* * * * *